United States Patent
Nakamura et al.

(10) Patent No.: US 10,130,449 B2
(45) Date of Patent: Nov. 20, 2018

(54) DENTAL CASTING BILLET MATERIAL, METAL POWDER FOR POWDER METALLURGY, DENTAL METAL COMPONENT, AND DENTAL PROSTHESIS

(71) Applicant: Seiko Epson Corporation, Tokyo (JP)

(72) Inventors: Hidefumi Nakamura, Hachinohe (JP); Teruo Anraku, Osaka (JP)

(73) Assignee: Seiko Epson Corporation (JP)

( * ) Notice: Subject to any disclaimer, the term of this patent is extended or adjusted under 35 U.S.C. 154(b) by 246 days.

(21) Appl. No.: 14/852,908

(22) Filed: Sep. 14, 2015

(65) Prior Publication Data
US 2016/0100920 A1    Apr. 14, 2016

(30) Foreign Application Priority Data
Oct. 9, 2014    (JP) .................................. 2014-208339

(51) Int. Cl.
| | | |
|---|---|---|
| *A61C 13/08* | (2006.01) | |
| *A61C 13/083* | (2006.01) | |
| *C22C 19/07* | (2006.01) | |
| *B22F 1/00* | (2006.01) | |
| *B22D 21/02* | (2006.01) | |

(52) U.S. Cl.
CPC ........ *A61C 13/0835* (2013.01); *A61C 13/081* (2013.01); *B22D 21/025* (2013.01); *B22F 1/0003* (2013.01); *C22C 19/07* (2013.01); *B22F 2301/15* (2013.01)

(58) Field of Classification Search
CPC ... A61C 13/00; A61C 13/0835; A61C 13/081; B22F 3/22; B22F 3/12; B22F 1/00; B22F 3/24; B22F 1/0003; B22F 2301/15; B22D 21/025; C22C 19/07
See application file for complete search history.

(56) References Cited

U.S. PATENT DOCUMENTS

| | | | | |
|---|---|---|---|---|
| 5,002,731 A | * | 3/1991 | Crook ..................... | C22C 19/07 148/425 |
| 2008/0232998 A1 | * | 9/2008 | Prasad ............... | A61C 13/0003 420/436 |
| 2011/0275031 A1 | * | 11/2011 | Jana .................... | A61C 13/0006 433/172 |
| 2012/0174404 A1 | * | 7/2012 | Wolz .................. | A61C 13/0003 29/896.1 |
| 2012/0244035 A1 | * | 9/2012 | Cascone ................. | C22C 30/00 420/583 |

(Continued)

FOREIGN PATENT DOCUMENTS

| | | |
|---|---|---|
| BG | 63728 B1 | 10/2002 |
| JP | 07-216484 A | 8/1995 |
| JP | 2001-510385 A | 7/2001 |

(Continued)

*Primary Examiner* — Nicholas Lucchesi
(74) *Attorney, Agent, or Firm* — Harness, Dickey & Pierce, P.L.C.

(57) ABSTRACT

A dental casting billet material includes: Co as a main component; Cr in a proportion of 26% by mass or more and 35% by mass or less; Mo in a proportion of 5% by mass or more and 12% by mass or less; and Si in a proportion of 0.3% by mass or more and 2.0% by mass or less, wherein the billet material is formed from a sintered body of a metal powder, and the billet material has a relative density of 92% or more and 99.5% or less.

7 Claims, 4 Drawing Sheets

(56) References Cited

U.S. PATENT DOCUMENTS

2013/0213802 A1* 8/2013 Sato .................. B22F 3/14
                                              204/298.13
2013/0224688 A1* 8/2013 Mayr ............... A61C 13/0004
                                              433/200.1

FOREIGN PATENT DOCUMENTS

JP     2006-328475 A    12/2006
WO     WO-99-29281 A2    6/1999

* cited by examiner

DENTAL CASTING BILLET MATERIAL, METAL POWDER FOR POWDER METALLURGY, DENTAL METAL COMPONENT, AND DENTAL PROSTHESIS

CROSS-REFERENCE TO RELATED APPLICATIONS

This application claims priority to Japanese Patent Application No. 2014-208339 filed on Oct. 9, 2014. The entire disclosures of Japanese Patent Application No. 2014-208339 is hereby incorporated herein by reference.

BACKGROUND

1. Technical Field

The present invention relates to a dental casting billet material, a metal powder for powder metallurgy, a dental metal component, and a dental prosthesis.

2. Related Art

When a tooth in the mouth is lost, by attaching a denture, mastication and vocalization can be maintained, or facial appearance can be fixed. The denture includes a denture base and an artificial tooth planted in the denture base. Among these, as the denture base, a metal base formed from a metal material and a resin base formed from a resin material are known. The metal base can be made sufficiently thin as compared with the resin base, and therefore has advantages that when the metal base is attached in the mouth, the sense of discomfort felt by a patient is reduced, or it is less likely to become an obstacle when a patient talks.

In addition, the metal base has a sufficiently high strength derived from a metal material. Due to this, the metal base also has advantages that it is difficult to bend and also it is less likely to adversely affect remaining teeth and gums when it is attached.

As a constituent material of such a metal base, for example, a cobalt-chromium alloy, a noble metal alloy, a titanium alloy, and the like are known. Among these, a cobalt-chromium alloy has relatively high chemical stability, and also is easily available, and therefore has been widely used.

JP-A-2006-328475 (PTL 1) discloses a Co—Cr alloy pellet having a composition of C (0.10% or more and 0.60% or less), Si (0.50% or more and 1.50% or less), Mn (0.05% or more and 0.50% or less), Cr (26.00% or more and 35.00% or less), Mo (4.00% or more and 7.00% or less), and N (0.30% or more and 1.60 or less).

When a metal base is produced by using a cobalt-chromium alloy, a lost-wax casting method is generally used. This method is performed as follows. First, a model which reproduces the shape in the mouth is produced. Subsequently, the shape of this model is copied into a wax. The thus obtained wax model is covered with a fire resistant material, followed by firing. By doing this, the wax model disappears, and a mold having a cavity corresponding to the wax model is obtained. Subsequently, a metal melt (molten metal) of a cobalt-chromium alloy is poured into the cavity of this mold, whereby a metal base having a desired shape is produced by casting.

In such a casting method, when a gap of the cavity is small, a metal melt sometimes cannot enter the cavity. When such a trouble occurs, a metal base having a desired shape cannot be produced. Due to this, in order to fill a metal melt in the cavity regardless of the shape of the cavity, the metal melt fluidity (flowability) needs to be high. However, the metal melt obtained by melting the Co—Cr alloy pellet disclosed in PTL 1 has low melt fluidity, and therefore, depending on the shape of the cavity, it is sometimes difficult to fill the metal melt in the cavity to every corner.

SUMMARY

An advantage of some aspects of the invention is to provide a dental casting billet material having excellent melt fluidity during casting, a metal powder for powder metallurgy capable of producing the dental casting billet material, a dental metal component produced by using the dental casting billet material, and a dental prosthesis produced by using the dental metal component.

The above advantage is achieved by the aspects of the invention described below.

A dental casting billet material according to an aspect of the invention contains Co as a main component, Cr in a proportion of 26% by mass or more and 35% by mass or less, Mo in a proportion of 5% by mass or more and 12% by mass or less, and Si in a proportion of 0.3% by mass or more and 2.0% by mass or less, and is formed from a sintered body of a metal powder, and has a relative density of 92% or more and 99.5% or less.

According to this, since the viscosity of a metal melt obtained by melting is small, a dental casting billet material having excellent melt fluidity during casting is obtained.

A dental casting billet material according to another aspect of the invention contains Ni as a main component, Cr in a proportion of 10% by mass or more and 30% by mass or less, Mo in a proportion of 5% by mass or more and 15% by mass or less, and Si in a proportion of 1.0% by mass or more and 3.0% by mass or less, and is formed from a sintered body of a metal powder, and has a relative density of 92% or more and 99.5% or less.

According to this, since the viscosity of a metal melt obtained by melting is small, a dental casting billet material having excellent melt fluidity during casting is obtained.

In the dental casting billet material according to the aspect of the invention, it is preferred that a part of the Si is contained as silicon oxide, and the ratio of Si contained as the silicon oxide to the Si is 10% by mass or more and 90% by mass or less.

According to this, a dental casting billet material which brings about favorable melt fluidity is obtained, and also a dental casting billet material capable of producing a cast product having favorable mechanical properties and also having favorable adhesiveness to porcelain is obtained.

In the dental casting billet material according to the aspect of the invention, it is preferred that the silicon oxide is segregated at the grain boundary of the sintered body.

According to this, since a metal melt having particularly favorable melt fluidity is obtained, even in the case where a gap of a cavity of a mold is small, a dental casting billet material capable of producing a cast product having high dimensional accuracy is obtained.

In the dental casting billet material according to the aspect of the invention, it is preferred that the average diameter of crystal structures is 3 μm or more and 50 μm or less.

According to this, the dental casting billet material becomes homogeneous, and therefore, melting is achieved from a surface layer to an inner layer without causing a large time lag. Due to this, a dental casting billet material having particularly high meltability and also having particularly favorable metal melt fluidity is obtained.

In the dental casting billet material according to the aspect of the invention, it is preferred that C is further contained in a proportion of 0.01% by mass or more and 0.09% by mass or less.

According to this, a dental casting billet material capable of producing a cast product having high mechanical properties is obtained. Further, when the dental casting billet material is melted, explosive boiling (bubbling) of the metal melt is difficult to occur. When explosive boiling of the metal melt occurs, casting failure is liable to occur, for example, a casting operation is impeded, air bubbles are liable to remain, etc., and therefore, suppression of explosive boiling is useful in the production of a high quality dental metal component.

In the dental casting billet material according to the aspect of the invention, it is preferred that the content of N is 0.3 times or more and 10 times or less of the content of C in terms of mass ratio.

According to this, both of the improvement of the mechanical properties of a dental metal component by the addition of C and the improvement of the metal melt fluidity by the addition of N can be achieved.

A metal powder for powder metallurgy according to still another aspect of the invention contains Co as a main component, Cr in a proportion of 26% by mass or more and 35% by mass or less, Mo in a proportion of 5% by mass or more and 12% by mass or less, and Si in a proportion of 0.3% by mass or more and 2.0% by mass or less, and is used for producing a dental casting billet material.

According to this, a metal powder for powder metallurgy capable of efficiently producing a dental casting billet material having particularly favorable melt fluidity is obtained.

A metal powder for powder metallurgy according to yet another aspect of the invention contains Ni as a main component, Cr in a proportion of 10% by mass or more and 30% by mass or less, Mo in a proportion of 5% by mass or more and 15% by mass or less, and Si in a proportion of 1.0% by mass or more and 3.0% by mass or less, and is used for producing a dental casting billet material.

According to this, a metal powder for powder metallurgy capable of efficiently producing a dental casting billet material having particularly favorable melt fluidity is obtained.

A dental metal component according to still yet another aspect of the invention contains Co as a main component, Cr in a proportion of 26% by mass or more and 35% by mass or less, Mo in a proportion of 5% by mass or more and 12% by mass or less, and Si in a proportion of 0.3% by mass or more and 2.0% by mass or less, and is obtained by melting and casting a dental casting billet material, which is formed from a sintered body of a metal powder, and has a relative density of 92% or more and 99.5% or less.

According to this, a favorable packing density during casting is obtained, and therefore, a dental metal component having high dimensional accuracy is obtained.

A dental metal component according to further another aspect of the invention contains Ni as a main component, Cr in a proportion of 10% by mass or more and 30% by mass or less, Mo in a proportion of 5% by mass or more and 15% by mass or less, and Si in a proportion of 1.0% by mass or more and 3.0% by mass or less, and is obtained by melting and casting a dental casting billet material, which is formed from a sintered body of a metal powder, and has a relative density of 92% or more and 99.5% or less.

According to this, a favorable packing density during casting is obtained, and therefore, a dental metal component having high dimensional accuracy is obtained.

A dental prosthesis according to still further another aspect of the invention includes the dental metal component according to the aspect of the invention and a porcelain layer provided on the surface of the dental metal component.

According to this, a dental prosthesis, in which the dental metal component and the porcelain layer are strongly adhered to each other so that the reliability is high, is obtained.

In the dental prosthesis according to the aspect of the invention, it is preferred that the porcelain layer contains alumina, and the dental prosthesis further has a mullite phase disposed between the dental metal component and the porcelain layer.

According to this, a dental prosthesis, in which the porcelain layer and the dental metal component are strongly adhered to each other through the mullite phase so that the porcelain layer is difficult to peel off, and thus the reliability is high, is obtained. Further, it is considered that due to the generation of the mullite phase, the wettability of a ceramic material to the dental metal component is improved during a firing treatment. Accordingly, also from such a viewpoint, the adhesiveness of the porcelain layer is considered to be enhanced.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, the dental casting billet material, the metal powder for powder metallurgy, the dental metal component, and the dental prosthesis according to the invention will be described in detail based on preferred embodiments shown in the accompanying drawings.

Dental Casting Billet Material

First, an embodiment of a dental casting billet material according to the invention and an embodiment of a metal powder for powder metallurgy according to the invention will be described. In the invention, an alloy material which has a specific composition and is used for dental casting is referred to as "dental casting billet material".

Figure 1:
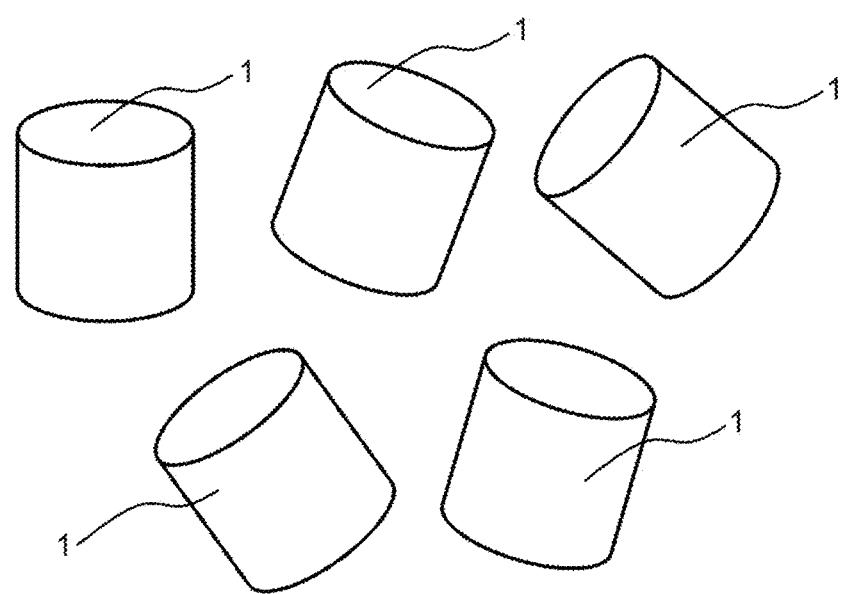
FIG. 1 is a perspective view showing an embodiment of a dental casting billet material according to the invention.

FIG. 1 is a perspective view showing an embodiment of a dental casting billet material according to the invention.

A dental casting billet material 1 (hereinafter also abbreviated and referred to as "billet material 1") shown in FIG. 1 is used for producing various cast products by being used for casting as a starting material. In the following description, as one example of the cast product, a case where a dental metal component is produced will be described.

The shape of the billet material 1 is not particularly limited, and may be a so-called irregular shape (an amorphous shape) or a particle, but is set to, for example, a spherical shape such as a true sphere or an elliptical sphere, a cylindrical shape such as a circular cylinder or a rectangular cylinder, a pyramidal shape such as a circular pyramid or a truncated pyramid, a polyhedral shape such as a cube, a cuboid, or an octahedron. In this embodiment, as one example, the billet material 1 in the shape of a circular cylinder as shown in FIG. 1 will be described.

Such a billet material 1 is formed from a Co—Cr—Mo—Si-based alloy or a Ni—Cr—Mo—Si-based alloy.

Specifically, the Co—Cr—Mo—Si-based alloy which forms the billet material 1 contains Co as a main component, Cr in a proportion of 26% by mass or more and 35% by mass or less, Mo in a proportion of 5% by mass or more and 12% by mass or less, and Si in a proportion of 0.3% by mass or more and 2.0% by mass or less.

On the other hand, the Ni—Cr—Mo—Si-based alloy which forms the billet material 1 contains Ni as a main component, Cr in a proportion of 10% by mass or more and 30% by mass or less, Mo in a proportion of 5% by mass or more and 15% by mass or less, and Si in a proportion of 1.0% by mass or more and 3.0% by mass or less.

These billet materials 1 are both formed from a sintered body of a metal powder and have a relative density of 92% or more and 99.5% or less.

When such a billet material 1 is, for example, used for casting and melted, the viscosity of the obtained metal melt (molten metal) is small, and therefore, the billet material 1 can give a metal melt having favorable melt fluidity. Due to this, even in the case where a shape in which a gap is small is contained in a cavity of a mold, the metal melt can be filled in the cavity to every corner. As a result, a cast body (a cast product) which reproduces the shape of the cavity more faithfully can be obtained. Therefore, in the case where the obtained cast body is applied to, for example, a dental metal component, a dental metal component which highly conforms to an affected part is obtained. As a result, the sense of discomfort when the dental metal component is attached can be reduced, and thus, the burden on a patient can be lightened.

Here, among the constituent elements of the billet material 1, Co (cobalt) or Ni (nickel) is a main component of the alloy which forms the billet material 1, and has a great effect on the basic properties of the billet material 1.

The content of Co is set to be the largest of the constituent elements of this billet material 1, and specifically the content of Co is preferably 50% by mass or more and 67.5% by mass or less, and more preferably 55% by mass or more and 67% by mass or less.

On the other hand, also the content of Ni is set to be the largest of the constituent elements of this billet material 1, and specifically the content of Ni is preferably 50% by mass or more and 67.5% by mass or less, and more preferably 55% by mass or more and 67% by mass or less.

Cr (chromium) mainly acts to improve the corrosion resistance of the billet material 1. It is considered that this is because by the addition of Cr, a passivation film (such as $Cr_2O_3$) is easily formed on the alloy, and thus, the chemical stability is improved. By the improvement of the corrosion resistance, the billet material 1 becomes less susceptible to the effect of the surrounding environment, and for example, even in the case where it is stored in a harsh environment, a metal melt having favorable melt fluidity can be realized. Further, by the improvement of the corrosion resistance, the meltability of the billet material 1 can also be enhanced. That is, by improving the corrosion resistance, a billet material 1 which can be melted promptly when it is heated to a predetermined temperature is obtained. By using such a billet material 1, a metal melt can be obtained in a short time, and therefore, the time required for casting can be reduced, and also the time in which the metal melt is oxidized can be minimized, and thus, an unintended change of the composition can be suppressed. Further, a dental metal component produced by using such a billet material 1 exhibits an effect that metal ions are difficult to be eluted even when the component comes in contact with, for example, a body fluid. Further, by using Cr along with Co (or Ni), Mo, and Si, the mechanical properties of the dental metal component can be enhanced.

The content of Cr in the alloy which forms the billet material 1 is set to 26% by mass or more and 35% by mass or less in the case of the Co—Cr—Mo—Si-based alloy, and is set to 10% by mass or more and 30% by mass or less in the case of the Ni—Cr—Mo—Si-based alloy. If the content of Cr is less than the above lower limit, the corrosion resistance of the billet material 1 is deteriorated. Therefore, the metal melt fluidity is deteriorated, or in the case where the dental metal component produced by casting is in contact with a body fluid over a long period of time, metal ions may be eluted. On the other hand, if the content of Cr exceeds the above upper limit, the amount of Cr with respect to Mo or Si is relatively too large, and therefore, the balance is lost, and thus, the mechanical properties of the dental metal component produced by casting are deteriorated.

The content of Cr is preferably set to 27% by mass or more and 34% by mass or less, and more preferably set to 28% by mass or more and 33% by mass or less in the case of the Co—Cr—Mo—Si-based alloy. On the other hand, in the case of the Ni—Cr—Mo—Si-based alloy, the content of Cr is preferably set to 12% by mass or more and 28% by mass or less, and more preferably set to 15% by mass or more and 25% by mass or less.

Mo (molybdenum) mainly acts to enhance the corrosion resistance of the billet material 1. That is, by the addition of Mo, the corrosion resistance improved by the addition of Cr can be further enhanced. It is considered that this is because by the addition of Mo, the passivation film containing a Cr oxide as a main material is further densified. Therefore, the Mo-added alloy particularly decreases the viscosity of a metal melt, and a metal melt having particularly favorable melt fluidity can be realized. In addition, metal ions are more difficult to be eluted, and thus, the addition of Mo contributes to the realization of a dental metal component having particularly high biocompatibility.

The content of Mo in the alloy which forms the billet material 1 is set to 5% by mass or more and 12% by mass or less in the case of the Co—Cr—Mo—Si-based alloy and is set to 5% by mass or more and 15% by mass or less in the case of the Ni—Cr—Mo—Si-based alloy. If the content of Mo is less than the above lower limit, the corrosion resistance of the billet material 1 may be insufficient. On the other hand, if the content of Mo exceeds the above upper limit, the amount of Mo with respect to Cr or Si is relatively too large, and therefore, the corrosion resistance may be deteriorated instead.

The content of Mo is preferably set to 5.5% by mass or more and 11% by mass or less, and more preferably set to 6% by mass or more and 9% by mass or less in the case of the Co—Cr—Mo—Si-based alloy. On the other hand, in the case of the Ni—Cr—Mo—Si-based alloy, the content of Mo is preferably set to 5.5% by mass or more and 13% by mass or less, and more preferably set to 6% by mass or more and 11% by mass or less.

Si (silicon) can improve the metal melt fluidity of the billet material 1. By the addition of Si, silicon oxide is formed by oxidizing a part of Si in the billet material 1. At least some of the oxygen atoms contained in the silicon oxide have been bonded to other metal elements. Therefore, Si can reduce oxides of other metal elements as a reducing agent. As a result, the degree of purification of the alloy which forms the billet material 1 can be increased, and the viscosity in melting can be decreased, and therefore, a metal melt having favorable melt fluidity can be obtained.

Further, Si enhances the mechanical properties of a dental metal component produced by casting using the billet material 1. By the addition of Si, silicon oxide is formed by oxidizing a part of Si in the billet material 1. Examples of the silicon oxide include SiO and $SiO_2$. Such silicon oxide is distributed in a dental metal component produced by casting using the billet material 1 such that it splits metal crystals. Accordingly, the metal crystal structure can be suppressed to be small, and thus, the mechanical properties of the dental metal component produced by casting can be further enhanced.

In addition, as described above, by increasing the degree of purification of the alloy which forms the billet material 1, a dental metal component produced by casting using the billet material 1 is blessed with excellent mechanical properties and chemical properties intrinsic to the alloy. Accordingly, also from such a viewpoint, the properties of the dental metal component produced by casting can be further enhanced.

Moreover, by the addition of Si, the adhesiveness of porcelain to a dental metal component produced by casting using the billet material 1 is improved. Therefore, when a porcelain layer is provided so as to cover the surface of the dental metal component, the peeling off of the porcelain layer is prevented, and thus, a dental prosthesis having high reliability is obtained.

In order to obtain the effect as described above, it is necessary to set the content of Si to 0.3% by mass or more and 2.0% by mass or less in the case of the Co—Cr—Mo—Si-based alloy, and 1.0% by mass or more and 3.0% by mass or less in the case of the Ni—Cr—Mo—Si-based alloy. If the content of Si is less than the above lower limit, the meltability of the billet material 1 is deteriorated, and also the metal melt fluidity is deteriorated. Further, the amount of silicon oxide is also decreased, and therefore, the size of a metal crystal is liable to increase in the billet material 1, and therefore, a possibility that the mechanical properties of a dental metal component produced by casting using the billet material 1 are also deteriorated is increased. Further, the adhesiveness of porcelain to the dental metal component also becomes insufficient, and therefore, a problem such as peeling off of the porcelain layer in a dental prosthesis is liable to occur. On the other hand, if the content of Si exceeds the above upper limit, the amount of silicon oxide present in the billet material 1 is too large, and a region where silicon oxide is spatially distributed in a continuous manner is liable to be formed. In such a region, the structure of the billet material 1 is discontinuous at a given size, and therefore, the meltability of the billet material 1 is deteriorated, and also the metal melt fluidity is deteriorated due to a large amount of silicon oxide. Further, the mechanical properties of the dental metal component produced by casting are deteriorated.

The content of Si is preferably set to 0.5% by mass or more and 1.0% by mass or less, and more preferably set to 0.6% by mass or more and 0.9% by mass or less in the case of the Co—Cr—Mo—Si-based alloy. On the other hand, in the case of the Ni—Cr—Mo—Si-based alloy, the content of Si is preferably set to 1.2% by mass or more and 2.8% by mass or less, and more preferably set to 1.5% by mass or more and 2.5% by mass or less.

Further, a part of the Si preferably exists in the form of silicon oxide as described above, however, as for the existing amount thereof, the ratio of Si contained as silicon oxide with respect to the total amount of Si is preferably 10% by mass or more and 90% by mass or less, more preferably 20% by mass or more and 80% by mass or less, further more preferably 30% by mass or more and 70% by mass or less, and particularly preferably 35% by mass or more and 65% by mass or less. By setting the ratio of Si contained as silicon oxide with respect to the total amount of Si within the above range, the effects such as favorable melt fluidity, favorable mechanical properties of a cast product, and favorable adhesiveness of porcelain as described above are more reliably brought about to the billet material 1.

Further, by setting the ratio of Si contained as silicon oxide in the Si within the above range, an appropriate hardness is imparted to a dental metal component produced by casting using the billet material 1. That is, it is considered that by the existence of a given amount of Si which is not in the form of silicon oxide, Si and at least one element selected from Co (or Ni), Cr, and Mo produce a hard intermetallic compound, which increases the hardness of the dental metal component. A dental prosthesis including the dental metal component having such a hardness is hardly deformed by a biting force after it is attached to an affected part, and thus, the reliability becomes high. In other words, by the addition of Si, significant growth of a metal crystal is inhibited, and therefore, from this viewpoint, although the hardness of the dental metal component tends to decrease, a part of Si forms an intermetallic compound, and therefore, a significant decrease in the hardness is prevented, and the reliability as a dental prosthesis can be ensured.

This intermetallic compound is not particularly limited, however, examples thereof include $CoSi_2$, $Cr_3Si$, $MoSi_2$, and $Mo_5Si_3$.

The ratio of Si contained as silicon oxide to the total amount of Si can be determined using gravimetry and ICP optical emission spectroscopy.

Further, in consideration of the deposition amount of the intermetallic compound, the ratio of the content of Si to the content of Mo (Si/Mo) is preferably 0.05 or more and 0.2 or less, and more preferably 0.08 or more and 0.15 or less in terms of mass ratio in the case of the Co—Cr—Mo—Si-based alloy. Further, in the case of the Ni—Cr—Mo—Si-based alloy, the ratio of the content of Si to the content of Mo (Si/Mo) is preferably 0.15 or more and 0.4 or less, and more preferably 0.2 or more and 0.35 or less in terms of mass ratio. According to this, the hardness of a dental metal component produced by using the billet material 1 can be optimized, and a dental prosthesis having high reliability can be obtained.

The silicon oxide may be distributed at any place, but is preferably distributed in a segregated manner at the grain boundary (the boundary surface between metal crystals). By segregating the silicon oxide at such a place, the degree of purification of the alloy which forms the metal crystal becomes particularly high. Due to this, when the billet material 1 in which silicon oxide is segregated at the grain boundary is used for, for example, casting and melted, the viscosity of the obtained metal melt is particularly decreased. Accordingly, a metal melt having particularly favorable melt fluidity can be provided. As a result, even in the case where a gap of a cavity of a mold is small, the metal melt can be filled in the cavity to every corner, and thus, a dental metal component having particularly high dimensional accuracy can be produced by casting.

In addition, by segregating silicon oxide at the grain boundary, as described above, the metal crystal structure can be made small, and also from this viewpoint, the meltability of the billet material 1 and the metal melt fluidity can be improved, and also the mechanical properties of the dental metal component can be further enhanced.

Further, the segregated silicon oxide deposits can be analyzed to specify the size, distribution, and the like thereof by an area analysis of a qualitative analysis. Specifically, in a compositional image of Si obtained using an electron probe microanalyzer (EPMA), an average diameter of a region where Si is segregated is preferably 0.1 μm or more and 10 μm or less, and more preferably 0.3 μm or more and 8 μm or less. When the average diameter of a region where Si is segregated is within the above range, the size of the silicon oxide deposit becomes most suitable for exhibiting the respective effects as described above. That is, if the average diameter of a region where Si is segregated is less than the above lower limit, the silicon oxide deposits are not segregated in a region having a sufficient size, and the above-mentioned respective effects may not be sufficiently obtained. On the other hand, if the average diameter of a region where Si is segregated exceeds the above upper limit, the viscosity of the metal melt is increased, and therefore, the melt fluidity of the billet material 1 may be deteriorated.

The average diameter of a region where Si is segregated can be determined as an average of the diameter of a circle having the same area (projected area circle equivalent diameter) as that of the region where Si is segregated in the compositional image of Si. Further, the average diameter of a region where Si is segregated is determined as an average of measurement values of 100 or more regions where Si is segregated.

Further, the billet material 1 formed from the Co—Cr—Mo—Si-based alloy includes a first phase formed mainly from Co and a second phase formed mainly from $Co_3Mo$. By including the second phase of these phases, an appropriate hardness is imparted to a dental metal component produced by casting using the billet material 1 in the same manner as the intermetallic compound containing Si described above, and therefore, a useful billet material 1 from the viewpoint of improvement of the reliability of a dental prosthesis is obtained. On the other hand, in the case where the second phase is included excessively, the second phase is liable to be segregated, and thus, the mechanical properties such as tensile strength, proof stress, and elongation may be deteriorated.

Therefore, it is preferred that the first phase and the second phase are included at an appropriate ratio from the above viewpoint. Specifically, for the billet material 1, a crystal structure analysis is performed by X-ray diffractometry using a Cu-Kα ray, and when the height of the highest peak among the peaks derived from Co is defined as 1, the height of the highest peak among the peaks derived from $Co_3Mo$ is preferably 0.01 or more and 0.5 or less, and more preferably 0.02 or more and 0.4 or less.

If the ratio of the height of the highest peak of $Co_3Mo$ to the height of the highest peak of Co, which is defined as 1, is less than the above lower limit, the ratio of $Co_3Mo$ to Co in the billet material 1 is decreased, and therefore, the hardness of a dental metal component produced by casting using the billet material 1 is decreased so that a dental prosthesis which is easily deformed by a biting force may be formed. On the other hand, if the ratio of the height of the highest peak of $Co_3Mo$ exceeds the above upper limit, the existing amount of $Co_3Mo$ is too large, and therefore, $Co_3Mo$ is liable to be segregated so that the tensile strength and the proof stress of the dental metal component are decreased, and also the elongation thereof may be decreased.

The Cu-Kα ray is generally a characteristic X-ray with an energy of 8.048 keV.

Further, when a peak derived from Co is identified, the identification is performed based on the database of Co of an ICDD (The International Centre for Diffraction Data) card. Similarly, when a peak derived from $Co_3Mo$ is identified, the identification is performed based on the database of $Co_3Mo$ of the ICDD card.

The billet material 1 has a relative density of 92% or more and 99.5% or less. The billet material 1 having such a relative density has a low content of an oxide or the like and also has excellent homogeneity. Due to this, a billet material 1 having excellent meltability is obtained. Further, the viscosity of the obtained metal melt becomes small, and therefore, a metal melt having favorable melt fluidity can be obtained, and thus, a dental metal component having high dimensional accuracy can be produced by casting.

If the relative density of the billet material 1 is lower than the above lower limit, the content of light elements such as an oxide is relatively increased, and therefore, such an element may impair the meltability of the billet material 1 or may impair the metal melt fluidity. On the other hand, if the relative density of the billet material 1 exceeds the above upper limit, it becomes difficult to stably produce homogeneous billet materials 1, and therefore, for example, a billet material 1 which has deteriorated meltability or deteriorated metal melt fluidity may be mixed.

The relative density thereof is preferably set to 93% or more and 99% or less, and more preferably set to 94% or more and 99% or less.

The relative density of the billet material 1 can be determined by measuring the density of the billet material 1, and also calculating the true density of the constituent material of the billet material 1, and then, calculating the ratio of the measured density of the billet material 1 to the true density.

The alloy which forms the billet material 1 may contain N (nitrogen) other than the elements as described above. N mainly acts to enhance the mechanical properties of a dental metal component produced by casting using the billet material 1. N is an austenitizing element, and therefore acts to enhance the toughness by accelerating the austenitization of the crystal structure of the dental metal component.

By the incorporation of N, the formation of a dendrite phase in the billet material 1 formed from a sintered body of a metal powder is prevented, and the content of the dendrite phase becomes very small. Therefore, also from this viewpoint, the toughness can be enhanced. In addition, since the formation of a dendrite phase is suppressed, the viscosity of the metal melt of the billet material 1 can be suppressed to be low, and thus, the metal melt fluidity can be improved.

Here, the dendrite phase is a dendritically grown crystal structure, and if a large amount of such a dendrite phase is contained, various problems may occur in a dental metal component produced by casting using the billet material 1. Therefore, the reduction of the content of the dendrite phase is effective. Specifically, the billet material 1 is observed with a scanning electron microscope, and in the obtained observation image, the ratio of the area occupied by the dendrite phase is preferably 20% or less, and more preferably 10% or less. When the billet material 1 satisfying such conditions is used for casting a dental metal component, a metal melt having a sufficiently low viscosity and favorable metal melt fluidity can be provided.

The billet material 1 is formed from a sintered body of a metal powder as described above. The metal powder has a high cooling rate and also has high cooling uniformity since the volume of each metal powder particle is very small. Therefore, in the billet material 1 formed from a sintered body of such a metal powder, the formation of a dendrite phase is prevented, and thus, the metal melt fluidity can be improved.

Further, by preventing the formation of a dendrite phase, also the meltability of the billet material 1 can be enhanced. According to this, a metal melt can be obtained in a short time using the billet material 1, and therefore, the time required for casting can be reduced, and also the time in which the metal melt is oxidized can be minimized, and thus, an unintended change of the composition can be suppressed.

The area ratio described above is calculated as a ratio of the area occupied by the dendrite phase to the area of the observation image, and the length of one side of the observation image is set to about 50 μm or more and 1000 μm or less.

In order to obtain the effect as described above, it is necessary to set the content of N to preferably 0.09% by mass or more and 0.5% by mass or less. If the content of N is less than the above lower limit, the austenitization of the crystal structure of the billet material 1 is insufficient depending on the composition of the alloy as a whole. Due to this, the melt fluidity of a metal melt obtained by using the billet material 1 may be deteriorated. It is considered that this is because in the billet material 1, other than the austenite phase ($\gamma$ phase), a large amount of an hcp structure ($\varepsilon$ phase) is deposited. On the other hand, if the content of N exceeds the above upper limit, various nitrides may be produced in a large amount. Therefore, the melt fluidity of a metal melt obtained by using the billet material 1 may be deteriorated.

The content of N is set to preferably 0.12% by mass or more and 0.4% by mass or less, more preferably 0.14% by mass or more and 0.25% by mass or less, and further more preferably 0.15% by mass or more and 0.22% by mass or less.

In particular, when the content of N is within the range of 0.15% by mass or more and 0.22% by mass or less, the austenite phase becomes particularly dominant, and the melt fluidity of the metal melt becomes particularly favorable, and also a remarkable improvement of the toughness of the dental metal component is observed. When the billet material 1 at this time is subjected to a crystal structure analysis by X-ray diffractometry using a Cr-K$\alpha$ ray, a very strong main peak derived from the austenite phase is observed. On the other hand, the heights of the peak derived from the hcp structure and the other peaks are all 5% or less of the height of the main peak. This proves that the austenite phase is dominant.

On the other hand, in the case of the Co—Cr—Mo—Si-based alloy, the ratio of the content of N to the content of Si (N/Si) is preferably 0.1 or more and 0.8 or less, and more preferably 0.2 or more and 0.6 or less in terms of mass ratio.

Further, in the case of the Ni—Cr—Mo—Si-based alloy, the ratio of the content of N to the content of Si (N/Si) is preferably 0.05 or more and 0.4 or less, and more preferably 0.1 or more and 0.3 or less in terms of mass ratio. According to this, both of the effect of improving the melt fluidity by the addition of Si and the effect of improving the melt fluidity by the addition of N are synergistically exhibited. It is considered that this is because the effect of increasing the degree of purification of the alloy to decrease the viscosity of the metal melt by the addition of an appropriate amount of Si and the effect of allowing the austenitization of the crystal structure to particularly proceed to decrease the viscosity of the metal melt by the addition of an appropriate amount of N are exhibited without cancelling each other out. As a result, a bullet material 1 having particularly favorable melt fluidity is obtained. Further, it is considered that one of the reasons why these two effects are synergistically exhibited is that while metal elements such as Si and Co (or Ni) form a substitutional solid solution, metal elements such as N and Co (or Ni) form an interstitial solid solution, and therefore, these metal elements can coexist with one another.

If the ratio of the content of N to the content of Si is less than the above lower limit, the austenitization of the crystal structure is difficult to proceed, and therefore, the above-mentioned synergistic effect may not be obtained. On the other hand, if the ratio exceeds the above upper limit, the alloy composition becomes a composition which is difficult to be sintered, and therefore, when the billet material 1 is produced by using the metal powder, the sintered density may not be sufficiently enhanced. As a result, the billet material 1 having a low density is produced. In such a billet material 1 having a low density, a pore having a relatively large diameter is easily mixed in the metal melt, and therefore, the pore is exploded during casting so that the shape of the dental metal component may be changed or a casting defect may be caused.

The alloy which forms the billet material 1 may also contain C (carbon) other than the elements as described above. By the addition of C, the mechanical properties of a dental metal component produced by casting using the billet material 1 can be further increased.

The content of C in the alloy which forms the billet material 1 is not particularly limited, but is preferably 0.01% by mass or more and 0.09% by mass or less, more preferably 0.01% by mass or more and 0.05% by mass or less, and further more preferably 0.01% by mass or more and 0.03% by mass or less. If the content of C exceeds the above upper limit, the brittleness of a dental metal component produced by casting using the billet material 1 is increased so that the mechanical properties may be deteriorated, and also when the billet material 1 is melted, explosive boiling (bubbling) of the metal melt may be easy to occur. On the other hand, if the content of C is less than the above lower limit, the mechanical properties of a dental metal component produced by casting using the billet material 1 may be deteriorated.

In the case of the Co—Cr—Mo—Si-based alloy, the content of C is preferably about 0.02 times or more and 0.5 times or less, and more preferably about 0.05 times or more and 0.3 times or less of the content of Si. Further, in the case of the Ni—Cr—Mo—Si-based alloy, the content of C is preferably about 0.008 times or more and 0.3 times or less, and more preferably about 0.02 times or more and 0.2 times or less of the content of Si. By setting the ratio of C to Si within the above range, the metal melt fluidity becomes particularly favorable. In addition, the mechanical properties of a dental metal component produced by casting using the billet material 1 can be particularly enhanced.

Further, the content of N is preferably about 0.3 times or more and 10 times or less, and more preferably about 2 times or more and 8 times or less of the content of C. By setting the ratio of N to C within the above range, both of the improvement of the mechanical properties of the dental metal component by the addition of C and the improvement of the metal melt fluidity by the addition of N can be achieved.

In addition, the alloy which forms the billet material 1 may include, other than the elements as described above, a small amount of an additive to be added deliberately within a range in which the above-mentioned effect is not impaired and an impurity inevitably generated during the production. In this case, the total content of the additive and the impurity is preferably set to 1% by mass or less, more preferably 0.5% by mass or less, and further more preferably 0.2% by mass or less. Examples of such an additive element and an impurity element include Li, B, N, O, Na, Mg, Al, P, S, Mn, K, Ca, Sc, Ti, V, Fe, Co, Ni, Zn, Ga, Ge, Y, Pd, Ag, In, Sn, Sb, Hf, Ta, W, Os, Ir, Pt, Au, and Bi.

The remainder of the alloy which forms the billet material 1 other than the elements as described above is Co or Ni. As described above, the content of Co or Ni is set to be the largest of the elements contained in the alloy which forms the billet material 1.

The respective constituent elements of the alloy which forms the billet material 1 and the compositional ratio thereof can be determined by, for example, Iron and steel—Atomic absorption spectrometric method specified in JIS G 1257 (2000), Iron and steel—ICP atomic emission spectrometric method specified in JIS G 1258 (2007), Iron and steel—Method for spark discharge atomic emission spectrometric analysis specified in JIS G 1253 (2002), Iron and steel—Method for X-ray fluorescence spectrometric analysis specified in JIS G 1256 (1997), gravimetric, titrimetric, and absorption spectrometric methods specified in JIS G 1211 to G 1237, or the like. Specifically, for example, an optical emission spectrometer for solids (spark optical emission spectrometer, model: SPECTROLAB, type: LAVMB08A) manufactured by SPECTRO Analytical Instruments GmbH can be used.

Incidentally, the methods specified in JIS G 1211 to G 1237 are as follows.

JIS G 1211 (2011): Iron and steel—Methods for determination of carbon content

JIS G 1212 (1997): Iron and steel—Methods for determination of silicon content

JIS G 1213 (2001): Iron and steel—Methods for determination of manganese content JIS G 1214 (1998): Iron and steel—Methods for determination of phosphorus content JIS G 1215 (2010): Iron and steel—Methods for determination of sulfur content JIS G 1216 (1997): Iron and steel—Methods for determination of nickel content JIS G 1217 (2005): Iron and steel—Methods for determination of chromium content JIS G 1218 (1999): Iron and steel—Methods for determination of molybdenum content JIS G 1219 (1997): Iron and steel—Methods for determination of copper content JIS G 1220 (1994): Iron and steel—Methods for determination of tungsten content JIS G 1221 (1998): Iron and steel—Methods for determination of vanadium content JIS G 1222 (1999): Iron and steel—Methods for determination of cobalt content JIS G 1223 (1997): Iron and steel—Methods for determination of titanium content JIS G 1224 (2001): Iron and steel—Methods for determination of aluminum content JIS G 1225 (2006): Iron and steel—Methods for determination of arsenic content JIS G 1226 (1994): Iron and steel—Methods for determination of tin content JIS G 1227 (1999): Iron and steel—Methods for determination of boron content JIS G 1228 (2006): Iron and steel—Methods for determination of nitrogen content JIS G 1229 (1994): Steel—Methods for determination of lead content JIS G 1232 (1980): Methods for determination of zirconium in steel JIS G 1233 (1994): Steel—Method for determination of selenium content JIS G 1234 (1981): Methods for determination of tellurium in steel JIS G 1235 (1981): Methods for determination of antimony in iron and steel JIS G 1236 (1992): Method for determination of tantalum in steel JIS G 1237 (1997): Iron and steel—Methods for determination of niobium content Further, when C (carbon) and S (sulfur) are determined, particularly, an infrared absorption method after combustion in a current of oxygen (after combustion in a high-frequency induction heating furnace) specified in JIS G 1211 (2011) is also used. Specifically, a carbon-sulfur analyzer, CS-200 manufactured by LECO Corporation can be used.

Further, when N (nitrogen) and O (oxygen) are determined, particularly, a method for determination of nitrogen content in iron and steel specified in JIS G 1228 (2006) and a method for determination of oxygen content in metallic materials specified in JIS Z 2613 (2006) are also used. Specifically, an oxygen-nitrogen analyzer, TC-300/EF-300 manufactured by LECO Corporation can be used.

The billet material 1 shown in FIG. 1 is formed from a sintered body of a metal powder, that is, it is produced by a powder metallurgy method. Such a billet material 1 produced by a powder metallurgy method is produced using a metal powder obtained by quenching (since the volume is small, it is easy to quench), and therefore, significant grain growth of a metal crystal is less likely to occur and therefore, the meltability and the metal melt fluidity of the billet material 1 can be particularly easily enhanced.

As the metal powder to be used for the production of the billet material 1, a powder formed from the alloy as described above is used. The average particle diameter thereof is preferably 3 μm or more and 100 μm or less, more preferably 4 μm or more and 80 μm or less, and further more preferably 5 μm or more and 60 μm or less. By using a metal powder having such a particle diameter, a billet material 1 which has particularly favorable meltability and metal melt fluidity can be obtained.

The average particle diameter is obtained as a particle diameter when the cumulative amount on a mass basis from the smaller particle diameter side in the particle size distribution obtained by laser diffractometry is 50%.

If the average particle diameter of the metal powder is less than the above lower limit, the moldability in powder metallurgy is deteriorated, and therefore, the density of the billet material 1 is decreased so that the meltability and the metal melt fluidity of the billet material 1 may be deteriorated. On the other hand, if the average particle diameter of the metal powder exceeds the above upper limit, the packing density of the metal powder in powder metallurgy is decreased, and therefore, also in this case, the density of the billet material 1 is decreased so that the problems as described above may occur.

Further, when the average particle diameter of the metal powder is within the above range, the maximum particle diameter of the metal powder is preferably 200 μm or less, and more preferably 150 μm or less. By controlling the maximum particle diameter of the metal powder within the above range, the density of the billet material 1 can be increased, and thus, the billet material 1 which has particularly favorable meltability and metal melt fluidity can be obtained.

Here, the "maximum particle diameter" refers to a particle diameter when the cumulative amount on a mass basis from the smaller particle diameter side in the particle size distribution obtained by laser diffractometry is 99.9%.

The average of the aspect ratio of the particle of the metal powder defined by PS/PL wherein PS (μm) represents the minor axis of each particle of the metal powder and PL (μm) represents the major axis thereof is preferably about 0.4 or more and 1 or less, and more preferably about 0.7 or more and 1 or less. The metal powder having such an aspect ratio has a shape relatively close to a spherical shape, and therefore, the packing factor when the powder is compact-molded is increased. As a result, a billet material 1 which has particularly favorable meltability and metal melt fluidity can be obtained.

Here, the "major axis" is the maximum length in the projected image of the particle, and the "minor axis" is the maximum length in the direction perpendicular to the major axis. Incidentally, the average of the aspect ratio is obtained as an average of measurement values of 100 or more particles of the metal powder.

On the other hand, the average of the aspect ratio in the cross section of the billet material 1 defined by CS/CL wherein CL represents the major axis of each crystal structure and CS represents the minor axis thereof is preferably about 0.4 or more and 1 or less, and more preferably about 0.5 or more and 1 or less. The crystal structure having such an aspect ratio has small anisotropy, and therefore is relatively easy to melt, and also the metal melt to be obtained has excellent melt fluidity.

Here, the "major axis" is the maximum length in one crystal structure in the observation image of the cross section of the billet material 1, and the "minor axis" is the maximum length in the direction perpendicular to the major axis. Incidentally, the average of the aspect ratio is obtained as an average of measurement values of 100 or more crystal structures.

The average diameter of the crystal structure of the billet material 1 is preferably about 3 μm or more and 50 μm or less, and more preferably about 5 μm or more and 40 μm or less. By controlling the average diameter of the crystal structure to fall within the above range, the billet material 1 becomes homogeneous, and therefore, melting can be achieved from the surface layer to the inner layer without causing a large time lag. Due to this, the billet material 1 is particularly easy to melt, and also a metal melt to be obtained has excellent melt fluidity.

The average diameter of the crystal structure of the billet material 1 can be determined as an average of the diameter of a circle having the same area (projected area circle equivalent diameter) as that of one crystal when observing the cross section of the billet material 1 with an electron microscope or a light microscope. At this time, an average of measurement values of 100 or more crystals is adopted.

It is preferred that the billet material 1 has mutually independent small pores therein. As having such pores, the billet material 1 has excellent melt fluidity. It is considered that this is because in the billet material 1 having mutually independent small pores, although the pores are contained, the pores are very small, and therefore, the pores are hardly exploded or hardly remain in the metal melt, so that the viscosity of the metal melt is difficult to decrease. It is also considered that besides that, the small pores enhance the meltability of the billet material 1. Accordingly, the billet material 1 having mutually independent small pores therein can achieve both meltability and metal melt fluidity.

The average diameter of the pores is preferably 0.1 μm or more and 10 μm or less, and more preferably 0.3 μm or more and 8 μm or less. When the average diameter of the pores is within the above range, a billet material 1 in which the meltability and the metal melt fluidity can be more highly achieved is obtained. That is, if the average diameter of the pores is less than the above lower limit, the meltability may be deteriorated, and on the other hand, if the average diameter of the pores exceeds the above upper limit, the pore in the metal melt is exploded or poured into a mold by heat, and therefore, a dental metal component having a desired shape may not be able to be produced.

The average diameter of the pores can be obtained as an average of the diameter of a circle having the same area as that of a pore (projected area circle equivalent diameter) in a scanning electron microscope image. Further, the average diameter of the pores is obtained as an average of measurement values of 100 or more pores.

The area ratio of the pores in the observation image of the billet material 1 is preferably 0.001% or more and 1% or less, and more preferably 0.005% or more and 0.5% or less. When the area ratio of the pores is within the above range, both of the meltability and the metal melt fluidity of the billet material 1 can be more highly achieved.

This area ratio is calculated as a ratio of the area of the pores to the area of the observation image, and the length of one side of the observation image is set to about 50 μm or more and 1000 μm or less.

Examples of the metal powder to be used for the production of the billet material 1 include those produced by a variety of powdering methods such as an atomization method (such as a water atomization method, a gas atomization method, or a spinning water atomization method), a reducing method, a carbonyl method, and a pulverization method.

Among these, a metal powder produced by an atomization method is preferably used, and a metal powder produced by a water atomization method or a spinning water atomization method is more preferably used. The atomization method is a method in which a molten metal (a metal melt) is caused to collide with a fluid (a liquid or a gas) sprayed at a high speed to atomize the metal melt into a fine powder and also to cool the fine powder, whereby a metal powder is produced. By producing the metal powder through such an atomization method, an extremely fine powder can be efficiently produced. Further, the shape of the particle of the obtained powder is closer to a spherical shape by the action of surface tension. Due to this, a molded body having a high packing factor is obtained when such a metal powder is molded by powder metallurgy. Accordingly, a billet material 1 having a high sintered density is obtained.

In the case where a water atomization method is used as the atomization method, the pressure of water (hereinafter referred to as "atomization water") to be sprayed to the molten metal is not particularly limited, but is preferably set to about 75 MPa or more and 120 MPa or less (750 kgf/cm$^2$ or more and 1200 kgf/cm$^2$ or less), and more preferably about 90 MPa or more and 120 MPa or less (900 kgf/cm$^2$ or more and 1200 kgf/cm$^2$ or less).

The temperature of the atomization water is also not particularly limited, but is preferably set to about 1° C. or higher and 20° C. or lower.

The atomization water is often sprayed in a cone shape such that it has a vertex on the fall path of the metal melt and the outer diameter gradually decreases downward. In this case, the vertex angle θ of the cone formed by the atomization water is preferably about 10° or more and 40° or less, and more preferably about 15° or more and 35° or less. According to this, a metal powder having a composition as described above can be reliably produced.

Further, by using a water atomization method (particularly, a spinning water atomization method), the metal melt can be particularly quickly cooled. Due to this, a billet material 1 which has excellent mechanical properties and machinability, and also is homogeneous, is obtained.

The cooling rate when cooling the metal melt in the atomization method is preferably 1×10$^{4°}$ C./s or more, and more preferably 1×10$^{5°}$ C./s or more. By the quick cooling in this manner, a metal powder in which the grain diameter of a metal crystal is particularly small is obtained.

Further, in the case where a molten metal is obtained by melting the starting material, when the melting point of the constituent material of the billet material 1 is represented by Tm, the melting temperature of the starting material is preferably set to about Tm+20° C. or higher and Tm+200° C. or lower, and more preferably set to about Tm+50° C. or higher and Tm+150° C. or lower. According to this, when a molten metal is finely atomized by colliding the molten metal with a fluid, it becomes easy to control the production of an alloy to be constant. That is, an alloy powder having a high purification degree (low oxygen content) is easily produced while preventing an increase in size of the crystal structure. Due to this, a metal powder particularly suitable for the production of the billet material 1 can be produced.

The thus obtained metal powder is molded by any of a variety of molding methods, whereby a molded body is obtained. Examples of the molding method include a press-molding method, an extrusion-molding method, and an injection-molding method.

Thereafter, the obtained molded body is degreased and fired, whereby a sintered body (billet material 1) is obtained. The firing temperature is appropriately set according to the composition of the alloy, but is set to, for example, about 900° C. or higher and 1400° C. or lower.

For the thus obtained sintered body, further an HIP treatment (hot isostatic pressing treatment) or the like may be performed.

The conditions for the HIP treatment are set, for example, as follows: the temperature is 850° C. or higher and 1200° C. or lower, and the time is about 1 hour or more and 10 hours or less.

Further, the pressure to be applied is preferably 50 MPa or more, and more preferably 100 MPa or more.

Incidentally, the billet material 1 is formed from a sintered body obtained by using a powder, in which N is solid-dissolved in a metal material from the time when the powder is produced. Therefore, in the billet material 1, N is substantially uniformly distributed, so that the physical properties thereof can be made substantially uniform. Accordingly, the homogeneity of the billet material 1 can be ensured, and excellent meltability is obtained, and also the viscosity of the metal melt becomes homogeneous, and therefore, the melt fluidity becomes particularly favorable.

Specifically, for example, in the cross section of the billet material 1, a place at a depth of 0.3 mm from the surface is defined as a surface layer portion, and a place at a depth of 5 mm from the surface is defined as an inner layer portion.

At this time, the concentration of N in the inner layer portion is preferably 50% or more and 200% or less, more preferably 60% or more and 175% or less, and further more preferably 75% or more and 150% or less of the concentration of N in the surface layer portion. If the concentration of N in the inner layer portion is less than the above lower limit or exceeds the above upper limit, the physical properties are different between the inner layer portion and the surface layer portion, and therefore, the meltability of the billet material 1 may be lowered, or the melt fluidity may be deteriorated.

The concentration of N in the inner layer portion and the surface layer portion can be determined based on a quantitative analysis of N using an electron probe microanalyzer (EPMA). At this time, by performing a linear analysis from the surface to an inner portion of the billet material 1, the N concentration distribution in the thickness direction of the billet material 1 can be obtained, and therefore, the concentration of N in the above-mentioned inner layer portion and surface layer portion can be efficiently determined.

It is considered that the homogeneity of such a billet material 1 is derived from the configuration that as described above, the billet material 1 is formed from a sintered body produced by powder metallurgy, and in addition to that, N is solid-dissolved in the metal material from the time when the powder is produced, and the billet material is formed from a sintered body produced by a powder metallurgy method using the powder. In order to solid-dissolve N in the metal material at the time when the powder is produced, for example, a method in which at least one element selected from Co (or Ni), Cr, Mo, and Si contained in the starting material is nitrided in advance, a method in which a molten metal (a metal melt) is maintained in a nitrogen gas atmosphere when or after the starting material is melted, a method in which nitrogen gas is injected (bubbled) in a molten metal, or the like is used.

Further, there is also a method in which a molded body obtained by molding the metal powder or a sintered body obtained by sintering the molded body is heated in a nitrogen gas atmosphere or is subjected to an HIP treatment in a nitrogen gas atmosphere, whereby the alloy is impregnated with nitrogen (a nitriding treatment). However, in this method, it is difficult to uniformly nitride the molded body or the sintered body from a surface layer portion to an inner layer portion. Even if nitriding can be performed, it is necessary to perform the treatment over an extremely long period of time while controlling the nitriding speed, and therefore, the method has a problem from the viewpoint of production efficiency of the billet material 1.

When the molded body obtained by using the powder in which N is solid-dissolved is degreased and fired, a variation in the concentration of solid-dissolved N can be suppressed by performing degreasing and firing in an inert gas such as nitrogen gas or argon gas.

It is considered that in the homogeneity of the billet material 1, the ratio of the content of N to the content of Si is involved other than the above configuration. That is, it is considered that when the N/Si is within the above range, the distortion of the crystal structure caused by solid-dissolving Si is suppressed by solid-dissolving N, and as a result, the homogeneity of the billet material 1 is enhanced.

By heating and melting the billet material 1 as described above and pouring the melted material into a mold, various cast products corresponding to the shape of the cavity of the mold can be produced.

Dental Metal Component

Next, an embodiment of the dental metal component according to the invention will be described.

The dental metal component according to the invention is not particularly limited as long as it is a metal component which is temporarily or semipermanently retained in the mouth, and examples thereof include metal frames such as an inlay, a crown, abridge, a metal base, a denture, an implant, an abutment, a fixture, and a screw. In the following description, a metal frame having a shape shown in FIG. 2 will be described as an example.

Here, in particular, a metal frame for porcelain bonding will be described, however, the metal frame according to the invention also includes metal frames which are not used for porcelain bonding, for example, an inlay, a crown, abridge, a metal base, a denture, an implant, an abutment, a fixture, a screw, and the like.

Figure 2:
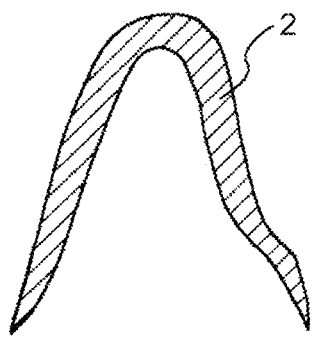
FIG. 2 is a longitudinal cross-sectional view showing a metal frame to which an embodiment of a dental metal component according to the invention is applied.

FIG. 2 is a longitudinal cross-sectional view showing a metal frame to which an embodiment of the dental metal component according to the invention is applied. A metal frame 2 shown in FIG. 2 is used as a base material for a dental prosthesis, and by providing a porcelain layer on the surface thereof, a dental prosthesis described later is formed.

For the metal frame 2 obtained by casting, a polishing treatment may be performed as needed. Examples of the polishing treatment include barrel polishing and sand blasting.

Further, for the obtained metal frame 2, a secondary process may be performed as needed. Examples of the secondary process include a machining process such as cutting and grinding, a laser process, an electron beam process, a water jet process, an electrical discharge process, a pressing process, an extrusion process, a rolling process, a forging process, a bending process, a squeezing process, a drawing process, a roll-forming process, and a shearing process.

The thus obtained metal frame 2 has high dimensional accuracy because it is obtained by casting using the metal melt of the billet material 1 having favorable melt fluidity as described above. Therefore, such a metal frame 2 can be attached to an affected part with less sense of discomfort, and thus, a burden on a patient can be minimized, and also when a porcelain layer is provided on the surface of the metal frame 2 as described later, high adhesiveness of the porcelain layer and high aesthetic appearance can be realized.

Further, the metal frame 2 has high corrosion resistance, and therefore has excellent biocompatibility.

Moreover, the metal frame 2 has excellent mechanical properties, and therefore is hardly deformed even by a biting force, and thus has excellent durability.

Dental Prosthesis

Next, an embodiment of a dental prosthesis according to the invention will be described.

Figure 3:
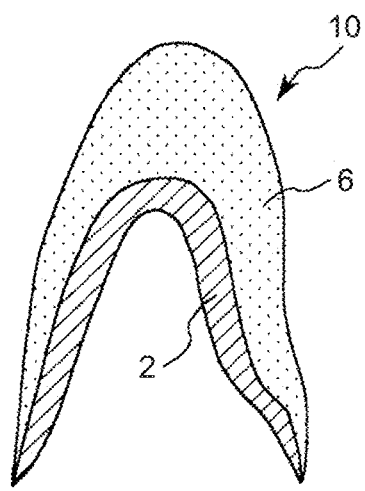
FIG. 3 is a longitudinal cross-sectional view showing an embodiment of a dental prosthesis according to the invention.

FIG. 3 is a longitudinal cross-sectional view showing an embodiment of a dental prosthesis according to the invention.

A dental prosthesis 10 shown in FIG. 3 includes a metal frame 2 and a porcelain layer 6 provided so as to cover a part of the surface of the metal frame 2.

The porcelain layer 6 is a member which plays a part in the aesthetic appearance of the dental prosthesis 10, and generally has a color close to the color of teeth.

Examples of a constituent material of the porcelain layer 6 include a variety of ceramic-based materials such as feldspar, quartz, porcelain clay, and a metal oxide and a variety of resin materials. Among these, from the viewpoint of aesthetic appearance and adhesiveness to the metal frame 2, a ceramic-based material is preferably used. Specific examples thereof include alumina, silica, lithium oxide, sodium oxide, potassium oxide, calcium oxide, iron oxide, magnesia, zirconia, titania, antimony oxide, and cerium oxide, and one type or a mixture of two or more types among these is used.

A slurry containing such a constituent material is applied to the surface of the metal frame 2, followed by a firing treatment, whereby the porcelain layer 6 is formed.

The constituent material of the porcelain layer 6 preferably contains alumina among these. When a ceramic material containing alumina is bonded to the surface of the metal frame 2 by firing, a mullite phase is generated in the vicinity of the boundary surface between the porcelain layer 6 and the metal frame 2. It is considered that this mullite phase is generated by mixing alumina contained in the ceramic material and Si or silicon oxide contained in the metal frame 2. Due to this, the porcelain layer 6 and the metal frame 2 are strongly adhered to each other through the mullite phase so that the porcelain layer 6 is hardly peeled off, and thus, a dental prosthesis having high reliability is obtained. Further, it is considered that due to the generation of the mullite phase, the wettability of the ceramic material to the metal frame 2 is improved during a firing treatment. Accordingly, from such a viewpoint, the adhesiveness of the porcelain layer 6 is considered to be enhanced, and moreover, the porcelain layer 6 can be fired and bonded evenly.

The content of alumina in the constituent material of the porcelain layer 6 is preferably about 2% by mass or more and 50% by mass or less, more preferably about 4% by mass or more and 35% by mass or less, and further more preferably about 6% by mass or more and 25% by mass or less. By setting the content of alumina within the above range, alumina necessary and sufficient for enhancing the adhesiveness between the porcelain layer 6 and the metal frame 2 is ensured, and also the mechanical properties of the porcelain layer 6 itself are enhanced, and thus, a dental prosthesis 10 having higher reliability is obtained.

If the content of alumina is less than the above lower limit, a sufficient amount of the mullite phase is not generated between the porcelain layer 6 and the metal frame 2, and therefore, the wettability of the ceramic material is deteriorated, and thus, the adhesiveness of the porcelain layer 6 may be deteriorated. On the other hand, if the content of alumina exceeds the above upper limit, the mechanical properties are liable to be deteriorated (for example, the porcelain layer 6 becomes brittle), and therefore, the adhesiveness of the porcelain layer 6 may be deteriorated just the same.

The average thickness of the porcelain layer 6 is not particularly limited, but is preferably about 0.05 mm or more and 3 mm or less, and more preferably about 0.2 mm or more and 2 mm or less. By setting the average thickness of the porcelain layer 6 within the above range, the adhesiveness of the porcelain layer 6 to the metal frame 2 can be further enhanced. Further, a necessary and sufficient light-shielding property is imparted to the porcelain layer 6, and therefore, the color of the metal frame 2 is hardly seen through the porcelain layer 6, and thus, the dental prosthesis 10 having excellent aesthetic appearance is obtained.

In the formation of the porcelain layer 6, first, the constituent material of the porcelain layer 6 is finely pulverized by a ball mill, a planetary mill, or the like. Thereafter, according to need, a heat treatment is performed at about 800° C. or higher and 1100° C. or lower for about 30 minutes or more and 60 minutes or less.

The thus obtained pulverized material is dispersed in a dispersion medium, whereby a material in the form of a slurry or a paste is prepared. In this manner, a slurry or a paste required for forming the porcelain layer 6 is obtained. Examples of the dispersion medium include water, propylene glycol, ethylene glycol, glycerin, polymethyl methacrylate, polyvinyl acetate, nitrocellulose, and ethyl cellulose.

The obtained slurry or paste is applied to the surface of the metal frame 2, and a firing treatment is performed. The firing temperature is appropriately set according to the constituent material of the porcelain layer 6, but is set to, for example, 500° C. or higher and 1000° C. or lower. In this manner, a dental prosthesis 10 is obtained.

Hereinabove, the dental casting billet material, the metal powder for powder metallurgy, the dental metal component, and the dental prosthesis according to the invention have been described with reference to preferred embodiments, however, the invention is not limited thereto.

For example, the dental metal component may be, for example, a screw, a bolt, a nut, a wire, or the like.

Examples

Next, specific examples of the invention will be described.

1. Production of Dental Casting Billet Material (Co-Based)
Sample No. 1

(1) First, a starting material was melted in a high-frequency induction furnace, and then powdered by a water atomization method, whereby a metal powder was obtained. Subsequently, the obtained metal powder was classified using a standard sieve having a mesh size of 150 μm. The alloy composition of the obtained metal powder is shown in Table 1. Incidentally, N was incorporated in the starting material in a state of being bonded to Cr (in a state of chromium nitride). In the determination of the alloy composition, an optical emission spectrometer for solids (a spark optical emission spectrometer) manufactured by SPECTRO Analytical Instruments GmbH (model: Spectrolab, type: LAVMB08A) was used. Further, in the quantitative analysis of C (carbon), a carbon/sulfur analyzer CS-200 manufactured by LECO Corporation was used.

(2) Subsequently, an organic binder was dissolved in water, whereby a binder solution was prepared. The amount of the organic binder in the binder solution was set to 10 g per kg of the metal powder. Further, the amount of water in the binder solution was set to 50 g per g of the organic binder.

(3) Subsequently, the metal powder was placed in a treatment vessel of a granulating device. Then, the metal powder was granulated by a spray drying method while spraying the binder solution from a spray nozzle of the granulating device onto the metal powder in the treatment vessel, whereby a granulated powder was obtained.

(4) Subsequently, by using the obtained granulated powder, molding was performed under the following molding conditions, whereby a molded body was obtained.
Molding Conditions:
Molding method: compact-molding
Molding pressure: 300 MPa (3 t/cm²)

(5) Subsequently, the obtained molded body was degreased under the following degreasing conditions, whereby a degreased body was obtained.
Degreasing Conditions
Heating temperature: 470° C.
Heating time: 1 hour
Heating atmosphere: nitrogen atmosphere (6) Subsequently, the obtained degreased body was fired under the following firing conditions, whereby a sintered body was obtained. The obtained sintered body was subjected to a machining process, whereby a dental casting billet material in the shape of a circular cylinder with a diameter of 15 mm and a length of 5 mm was obtained.
Firing Conditions
Heating temperature: 1300° C.
Heating time: 3 hours
Heating atmosphere: argon atmosphere
Sample Nos. 2 to 16

Dental casting billet materials were obtained in the same manner as in the case of the sample No. 1 except that the production conditions were changed as shown in Table 1, respectively.
Sample Nos. 17 to 20

When a starting material was melted in a high-frequency induction furnace, nitrogen gas was injected into the molten metal. At this time, by appropriately changing the injection time, the content of N was changed.

Then, dental casting billet materials were obtained in the same manner as in the case of the sample No. 1 except that the production conditions other than this were changed as shown in Table 1, respectively.

Examples 21 to 24

First, metal powders were obtained in the same manner as in the case of the sample No. 1 by using a starting material containing no N, respectively.

Subsequently, sintered bodies were obtained in the same manner as in the case of the sample No. 1 except that each of the obtained metal powders was used, and also the heating atmosphere in the firing conditions was changed to a mixed gas atmosphere containing argon at 50% by volume and nitrogen at 50% by volume. At this time, by appropriately changing the partial pressure of nitrogen gas, the content of N to be contained in the metal powder was changed.

Then, dental casting billet materials were obtained in the same manner as in the case of the sample No. 1 except that the production conditions other than this were changed as shown in Table 1, respectively.
Sample Nos. 25 and 26

When a starting material was melted in a high-frequency induction furnace, nitrogen gas was injected into the molten metal. At this time, by appropriately changing the injection time, the content of N to be contained in the metal powder was changed.

Then, dental casting billet materials were obtained in the same manner as in the case of the sample No. 1 except that the production conditions other than this were changed as shown in Table 1, respectively.
Sample Nos. 27 to 29

When a starting material was melted in a high-frequency induction furnace, nitrogen gas was injected into the molten metal. Thereafter, the molten metal was poured into a mold in the shape of a billet material, whereby a cast body was obtained. At this time, by appropriately changing the injection time, the content of N to be contained in the metal powder was changed.

Then, dental casting billet materials were obtained in the same manner as in the case of the sample No. 1 except that the production conditions other than this were changed as shown in Table 1, respectively.

The production conditions for the dental casting billet materials (Co-based) of the above-mentioned respective sample Nos. are shown in Tables 1 and 2.

TABLE 1

| | | Dental casting billet material Alloy composition | | | | | | |
|---|---|---|---|---|---|---|---|---|
| | | Cr | Mo | Si | C Mass % | N | Ni | Co |
| Sample No. 1 | Example | 29.8 | 6.80 | 0.78 | 0.02 | 0.13 | 0.01 | Remainder |
| Sample No. 2 | Example | 27.3 | 8.43 | 0.96 | 0.04 | 0.18 | 0.01 | Remainder |
| Sample No. 3 | Example | 28.5 | 7.21 | 0.83 | 0.03 | 0.12 | 0.01 | Remainder |
| Sample No. 4 | Example | 26.1 | 5.32 | 0.34 | 0.02 | 0.09 | 0.01 | Remainder |
| Sample No. 5 | Example | 31.9 | 6.50 | 0.71 | 0.07 | 0.23 | 0.01 | Remainder |
| Sample No. 6 | Example | 33.5 | 9.27 | 0.65 | 0.13 | 0.28 | 0.01 | Remainder |
| Sample No. 7 | Example | 34.9 | 11.80 | 0.95 | 0.35 | 0.27 | 0.01 | Remainder |
| Sample No. 8 | Example | 27.1 | 5.49 | 0.96 | 0.07 | 0.11 | 0.01 | Remainder |
| Sample No. 9 | Example | 26.1 | 5.11 | 0.83 | 0.04 | 0.12 | 0.02 | Remainder |
| Sample No. 10 | Example | 29.9 | 10.75 | 0.65 | 1.19 | 0.21 | 0.02 | Remainder |
| Sample No. 11 | Example | 29.8 | 6.80 | 0.78 | 0.05 | 0.26 | 0.01 | Remainder |
| Sample No. 12 | Example | 27.3 | 8.43 | 0.96 | 0.04 | 0.36 | 0.01 | Remainder |
| Sample No. 13 | Example | 28.5 | 7.21 | 0.83 | 0.03 | 0.24 | 0.01 | Remainder |
| Sample No. 14 | Example | 26.1 | 5.32 | 0.54 | 0.00 | 0.18 | 0.01 | Remainder |
| Sample No. 15 | Example | 27.5 | 5.84 | 0.34 | 0.02 | 0.11 | 0.01 | Remainder |
| Sample No. 16 | Example | 26.1 | 7.24 | 1.23 | 0.02 | 0.31 | 0.01 | Remainder |
| Sample No. 17 | Example | 31.9 | 6.50 | 0.71 | 0.03 | 0.46 | 0.01 | Remainder |
| Sample No. 18 | Example | 27.1 | 5.49 | 1.45 | 0.07 | 0.35 | 0.01 | Remainder |
| Sample No. 19 | Example | 26.1 | 5.11 | 0.83 | 0.04 | 0.31 | 0.02 | Remainder |
| Sample No. 20 | Example | 29.9 | 6.52 | 0.65 | 1.19 | 0.42 | 0.02 | Remainder |
| Sample No. 21 | Example | 29.1 | 5.88 | 0.71 | 0.02 | 0.01 | 0.01 | Remainder |
| Sample No. 22 | Example | 32.4 | 6.78 | 0.99 | 0.06 | 0.03 | 0.02 | Remainder |
| Sample No. 23 | Example | 33.5 | 9.27 | 0.65 | 0.13 | 0.56 | 0.01 | Remainder |
| Sample No. 24 | Example | 34.9 | 11.80 | 0.95 | 0.35 | 0.54 | 0.01 | Remainder |
| Sample No. 25 | Example | 32.2 | 6.87 | 0.78 | 0.05 | 0.03 | 0.02 | Remainder |
| Sample No. 26 | Example | 32.6 | 7.85 | 0.86 | 0.08 | 0.65 | 0.01 | Remainder |
| Sample No. 27 | Comp. Ex. | 29.2 | 6.11 | 0.65 | 0.04 | 0.32 | 0.02 | Remainder |
| Sample No. 28 | Comp. Ex. | 27.9 | 5.82 | 0.69 | 0.02 | 0.45 | 0.03 | Remainder |
| Sample No. 29 | Comp. Ex. | 30.1 | 6.99 | 0.61 | 0.05 | 0.39 | 0.10 | Remainder |

TABLE 2

| | | Dental casting billet material | | | | | |
|---|---|---|---|---|---|---|---|
| | | Alloy composition | | | | | |
| | | Si/Mo | C/Si | N/Si | N/C | N impregnation method | Molding method |
| Sample No. 1 | Example | 0.115 | 0.026 | 0.167 | 6.50 | Nitriding of metal material | Powder metallurgy |
| Sample No. 2 | Example | 0.114 | 0.042 | 0.188 | 4.50 | Nitriding of metal material | Powder metallurgy |
| Sample No. 3 | Example | 0.115 | 0.036 | 0.145 | 4.00 | Nitriding of metal material | Powder metallurgy |
| Sample No. 4 | Example | 0.064 | 0.059 | 0.265 | 4.50 | Nitriding of metal material | Powder metallurgy |
| Sample No. 5 | Example | 0.109 | 0.099 | 0.324 | 3.29 | Nitriding of metal material | Powder metallurgy |
| Sample No. 6 | Example | 0.070 | 0.200 | 0.431 | 2.15 | Nitriding of metal material | Powder metallurgy |
| Sample No. 7 | Example | 0.081 | 0.368 | 0.284 | 0.77 | Nitriding of metal material | Powder metallurgy |
| Sample No. 8 | Example | 0.175 | 0.073 | 0.115 | 1.57 | Nitriding of metal material | Powder metallurgy |
| Sample No. 9 | Example | 0.162 | 0.048 | 0.145 | 3.00 | Nitriding of metal material | Powder metallurgy |
| Sample No. 10 | Example | 0.060 | 1.831 | 0.323 | 0.18 | Nitriding of metal material | Powder metallurgy |
| Sample No. 11 | Example | 0.115 | 0.064 | 0.333 | 5.20 | Nitriding of metal material | Powder metallurgy |
| Sample No. 12 | Example | 0.114 | 0.042 | 0.375 | 9.00 | Nitriding of metal material | Powder metallurgy |
| Sample No. 13 | Example | 0.115 | 0.036 | 0.289 | 8.00 | Nitriding of metal material | Powder metallurgy |
| Sample No. 14 | Example | 0.102 | 0.000 | 0.333 | — | Nitriding of metal material | Powder metallurgy |
| Sample No. 15 | Example | 0.058 | 0.059 | 0.324 | 5.50 | Nitriding of metal material | Powder metallurgy |
| Sample No. 16 | Example | 0.170 | 0.016 | 0.252 | 15.50 | Nitriding of metal material | Powder metallurgy |
| Sample No. 17 | Example | 0.109 | 0.042 | 0.648 | 15.33 | Injection into metal melt | Powder metallurgy |
| Sample No. 18 | Example | 0.264 | 0.048 | 0.241 | 5.00 | Injection into metal melt | Powder metallurgy |
| Sample No. 19 | Example | 0.162 | 0.048 | 0.373 | 7.75 | Injection into metal melt | Powder metallurgy |
| Sample No. 20 | Example | 0.100 | 1.831 | 0.646 | 0.35 | Injection into metal melt | Powder metallurgy |
| Sample No. 21 | Example | 0.121 | 0.028 | 0.014 | 0.50 | Nitriding during sintering | Powder metallurgy |
| Sample No. 22 | Example | 0.146 | 0.061 | 0.030 | 0.50 | Nitriding during sintering | Powder metallurgy |
| Sample No. 23 | Example | 0.070 | 0.200 | 0.862 | 4.31 | Nitriding during sintering | Powder metallurgy |
| Sample No. 24 | Example | 0.081 | 0.368 | 0.568 | 1.54 | Nitriding during sintering | Powder metallurgy |
| Sample No. 25 | Example | 0.114 | 0.064 | 0.038 | 0.60 | Injection into metal melt | Powder metallurgy |

TABLE 2-continued

|  |  | Dental casting billet material | | | | | |
|---|---|---|---|---|---|---|---|
|  |  | Alloy composition | | | | | |
|  |  | Si/Mo | C/Si | N/Si | N/C | N impregnation method | Molding method |
| Sample No. 26 | Example | 0.110 | 0.093 | 0.756 | 8.13 | Injection into metal melt | Powder metallurgy |
| Sample No. 27 | Comp. Ex. | 0.106 | 0.062 | 0.492 | 8.00 | Injection into metal melt | Casting |
| Sample No. 28 | Comp. Ex. | 0.119 | 0.029 | 0.652 | 22.50 | Injection into metal melt | Casting |
| Sample No. 29 | Comp. Ex. | 0.087 | 0.082 | 0.639 | 7.80 | Injection into metal melt | Casting |

In the respective tables, among the metal powders and the dental casting billet materials of the respective sample Nos., those corresponding to the invention are indicated by "Example", and those not corresponding to the invention are indicated by "Comp. Ex." (Comparative Example).

2. Evaluation of Dental Casting Billet Material (Co-Based)

2.1 Measurement of Relative Density

With respect to each of the dental casting billet materials of the respective sample Nos., first, the density was measured in accordance with the method specified in JIS Z 8807 (2012).

Subsequently, the true density was calculated based on the compositional ratio of each of the dental casting billet materials of the respective sample Nos.

Then, the ratio of the measured density to the calculated true density was calculated and determined as the relative density of the dental casting billet material.

2.2 Measurement of Crystal Grain Diameter

Each of the dental casting billet materials of the respective sample Nos. was polished, and the obtained polished surface was observed with a scanning electron microscope. Then, for 100 crystals selected at random from the observation image, the projected area circle equivalent diameter was measured, and the data of the 100 crystals was averaged. The thus obtained average was defined as the crystal grain diameter of each of the dental casting billet materials of the respective sample Nos.

2.3 Measurement of Total Amount of Si and Content of Si Contained as Silicon Oxide With respect to each of the dental casting billet materials of the respective sample Nos., the total amount of Si and the content of Si contained as silicon oxide were measured by gravimetry and ICP optical emission spectroscopy, and the ratio of the amount of Si contained as silicon oxide to the total amount of Si was calculated. The calculation results are shown in Table 3.

2.4 Evaluation of Crystal Structure by X-Ray Diffractometry

With respect to each of the dental casting billet materials of the respective sample Nos., a crystal structure analysis was performed by X-ray diffractometry. Then, the height and the position of each peak contained in an obtained X-ray diffraction pattern were collated with the database listed in the ICDD card, whereby the crystal structure contained in the dental casting billet material was identified. Then, the ratio of the height of the highest peak among the peaks derived from $Co_3Mo$ was calculated when the height of the highest peak among the peaks derived from Co was defined as 1. The calculation results are shown in Table 3.

2.5 Evaluation of Pore, Dendrite Phase, and Aspect Ratio of Crystal Structure

Each of the dental casting billet materials of the respective sample Nos. was polished, and the obtained polished surface was observed with a scanning electron microscope, and a region occupied by a pore in the observation image was specified. Then, the average diameter of the region occupied by a pore (this is regarded as the average diameter of a pore) was measured, and also the ratio of the area of the region occupied by a pore to the total area of the observation image (area ratio) was calculated.

Further, by confirming the degree of existence of a dendritic structure in the observation image, the degree of existence of a dendrite phase was evaluated according to the following evaluation criteria.

Evaluation Criteria for Dendrite Phase

A: Almost no dendrite phase exists.

B: A dendrite phase exists in a slight amount (at an area ratio of 10% or less).

C: A dendrite phase exists in a somewhat large amount (at an area ratio of more than 10% and 20% or less).

D: A dendrite phase exists in a large amount (at an area ratio of more than 20%).

Further, the obtained polished surface was observed with a scanning electron microscope, and an average of the aspect ratio of a crystal structure in the observation image was calculated.

The above evaluation results are shown in Table 3.

2.6 Evaluation of Concentration of N

Each of the dental casting billet materials of the respective sample Nos. was cut and the cut surface was polished.

Subsequently, a linear analysis was performed by an electron probe microanalyzer (EPMA) from the surface to an inner portion in the polished surface. Then, the concentration distribution from the surface to the inner portion was determined.

Then, the concentration of N at a position of 0.3 mm from the surface was determined as the concentration of N in a surface layer portion, and the concentration of N at a position of 5 mm from the surface was determined as the concentration of N in an inner layer portion, and the ratio of the concentration of N in the inner layer portion to the concentration of N in the surface layer portion was calculated. The calculation results are shown in Table 3.

2.7 Measurement of Vickers Hardness

Each of the dental casting billet materials of the respective sample Nos. was cut and the cut surface was polished.

Subsequently, the Vickers hardness at a position of 0.3 mm from the surface of the billet material in the polished surface was measured and determined as the Vickers hardness of a surface layer portion. Further, the Vickers hardness at a position of 5 mm from the surface of the billet material was measured and determined as the Vickers hardness of an inner layer portion.

Then, the ratio of the Vickers hardness of the inner layer portion to the Vickers hardness of the surface layer portion was calculated. The calculation results are shown in Table 3.

Incidentally, a testing load with a diamond indenter was set to 100 gf.

2.8 Evaluation of Corrosion Resistance

A test piece was cut out by a machining process from each of the dental casting billet materials of the respective sample Nos.

Subsequently, with respect to each of the obtained test pieces, the amount of eluted metal ions was measured in accordance with the test method for corrosion resistance of a noble metal material for dental metal-ceramic restoration specified in JIS T 6118 (2012).

Then, the measurement results were evaluated according to the following evaluation criteria.

Evaluation Criteria for Corrosion Resistance

A: The corrosion resistance is very high (the amount of eluted metal ions is very small).

B: The corrosion resistance is high (the amount of eluted metal ions is small).

C: The corrosion resistance is low (the amount of eluted metal ions is large).

D: The corrosion resistance is very low (the amount of eluted metal ions is very large).

The above evaluation results are shown in Table 4.

2.9 Evaluation of Meltability 2.9.1 Time Required for Melting

Each of the dental casting billet materials of the respective sample Nos. was melted in a high-frequency induction heating furnace. Then, the meltability of the billet material was evaluated by comparing a time required for melting from when the billet material began to melt until when the billet material completely melted. In the evaluation, the evaluation was performed according to the following relative evaluation criteria.

Evaluation Criteria for Meltability

A: The meltability is very high (the time required for melting is very short).

B: The meltability is high (the time required for melting is short).

C: The meltability is low (the time required for melting is long).

D: The meltability is very low (the time required for melting is very long).

2.9.2 Ease of Occurrence of Explosive Boiling of Metal Melt

Each of the dental casting billet materials of the respective sample Nos. was melted in a high-frequency induction heating furnace. Then, the ease of occurrence of explosive boiling of the obtained metal melt was evaluated according to the following relative evaluation criteria.

Evaluation Criteria for Ease of Occurrence of Explosive Boiling of Metal Melt

A: Explosive boiling of the metal melt is very easy to occur (the frequency of occurrence of explosive boiling per unit time is very high).

B: Explosive boiling of the metal melt is easy to occur (the frequency of occurrence of explosive boiling per unit time is high).

C: Explosive boiling of the metal melt is difficult to occur (the frequency of occurrence of explosive boiling per unit time is low).

D: Explosive boiling of the metal melt is very difficult to occur (the frequency of occurrence of explosive boiling per unit time is very low).

2.10 Evaluation of Metal Melt Fluidity

Each of the dental casting billet materials of the respective sample Nos. was melted in a high-frequency induction heating furnace. Then, the obtained metal melt was cast into a mold. Thereafter, the mold was removed, and the cast product was taken out.

Figure 4A:
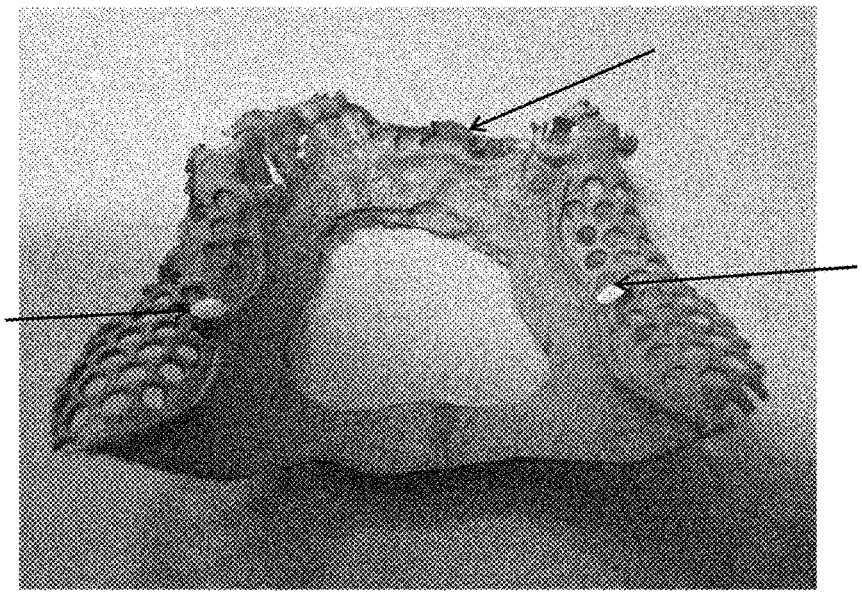
FIG. 4A is a photograph showing one example of a cast product formed by casting a metal melt obtained using each of dental casting billet materials of respective sample Nos.

FIG. 4A is a photograph showing one example of the cast product formed by casting the metal melt obtained using each of the dental casting billet materials of the respective sample Nos. The three arrows shown in FIG. 4A indicate the positions of the casting ports.

Figure 4B:
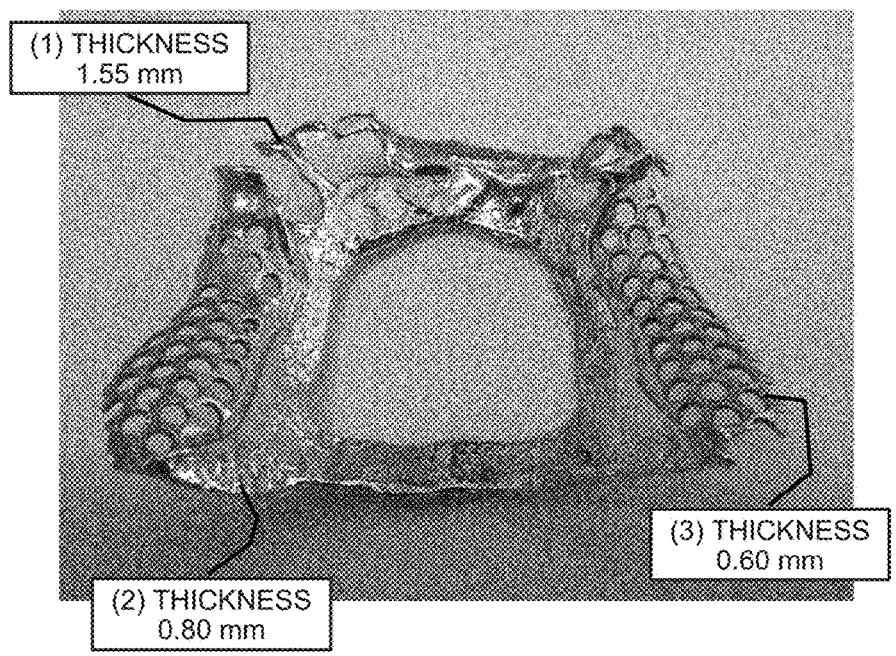
FIG. 4B is a photograph showing one example of a metal base obtained by removing a portion corresponding to a melt passage from the cast product shown in FIG. 4A.

FIG. 4B is a photograph showing one example of a metal base obtained by removing a portion corresponding to a melt passage from the cast product shown in FIG. 4A.

Subsequently, the obtained metal base was observed and evaluated as to whether or not casting failure derived from the metal melt fluidity such as uncast or a weld line occurs in portions shown in (1) to (3) in the metal base shown in FIG. 4B. The evaluation of casting failure was performed based on the following evaluation criteria for 20 metal bases obtained in the same manner. Incidentally, the portions (1) to (3) are different from each other in the thickness, and the thickness of the portion (1) is 1.55 mm, the thickness of the portion (2) is 0.80 mm, and the thickness of the portion (3) is 0.60 mm.

Evaluation Criteria for Casting Failure

A: The rate of occurrence of casting failure in the portion (3) is 3/20 or less.

B: The rate of occurrence of casting failure in the portion (3) is 4/20 or more and 6/20 or less.

C: The rate of occurrence of casting failure in the portion (2) is 1/20 or more and 3/20 or less.

D: The rate of occurrence of casting failure in the portion (2) is 4/20 or more.

3. Evaluation of Cast Product 3.1 Evaluation of 0.2% Proof Stress, Elongation, and Young's Modulus Each of the dental casting billet materials of the respective sample Nos. was melted, and the obtained metal melt was cast into a mold, whereby a test piece was produced by casting.

Subsequently, for the obtained test pieces, the 0.2% proof stress and elongation were measured in accordance with the test method for mechanical properties of a noble metal material for dental metal-ceramic restoration specified in JIS T 6118 (2012).

Further, the Young's modulus was determined in accordance with the test method for a dental metal material specified in JIS T 6004 (2012).

The measurement results are shown in Table 4.

3.2 Evaluation of Castability (Entire Appearance)

The shape of each of the obtained test pieces was observed with the eye and a magnifying glass, and the presence or absence of a casting defect (entire appearance) was evaluated according to the following evaluation criteria.

Evaluation Criteria for Casting Defect

A: A blow hole having a maximum length of more than 0.3 mm is not observed.

B: A blow hole having a maximum length of more than 0.5 mm is not observed.

C: A blow hole having a maximum length of more than 1 mm is not observed.

D: A blow hole having a maximum length of more than 1 mm is observed.

TABLE 3

Dental casting billet material Evaluation results

| | | Relative density % | Crystal grain diameter μm | SiO$_2$/ total Si % | Ratio of height of peak in XRD — | Pore Average diameter μm | Pore Area ratio % | Inner layer portion/surface layer portion N concentration % | Inner layer portion/surface layer portion Hardness % | Dendrite phase — | Aspect ratio — |
|---|---|---|---|---|---|---|---|---|---|---|---|
| Sample No. 1  | Example   | 96 | 7  | 53 | 0.22 | 0.53 | 0.025 | 108 | 98  | B | 0.72 |
| Sample No. 2  | Example   | 97 | 6  | 36 | 0.31 | 0.66 | 0.038 | 126 | 96  | A | 0.65 |
| Sample No. 3  | Example   | 96 | 7  | 45 | 0.27 | 0.58 | 0.032 | 92  | 102 | B | 0.58 |
| Sample No. 4  | Example   | 95 | 12 | 24 | 0.25 | 0.74 | 0.051 | 75  | 105 | C | 0.46 |
| Sample No. 5  | Example   | 99 | 5  | 49 | 0.38 | 0.35 | 0.022 | 135 | 95  | A | 0.82 |
| Sample No. 6  | Example   | 98 | 6  | 32 | 0.42 | 0.89 | 0.087 | 112 | 97  | A | 0.42 |
| Sample No. 7  | Example   | 95 | 9  | 28 | 0.48 | 0.97 | 0.097 | 173 | 88  | A | 0.41 |
| Sample No. 8  | Example   | 93 | 11 | 66 | 0.16 | 0.45 | 0.121 | 70  | 115 | C | 0.75 |
| Sample No. 9  | Example   | 95 | 15 | 77 | 0.36 | 0.43 | 0.112 | 98  | 101 | B | 0.77 |
| Sample No. 10 | Example   | 92 | 24 | 55 | 0.63 | 0.75 | 0.089 | 103 | 99  | A | 0.43 |
| Sample No. 11 | Example   | 99 | 4  | 53 | 0.22 | 0.53 | 0.025 | 111 | 97  | A | 0.73 |
| Sample No. 12 | Example   | 98 | 7  | 36 | 0.31 | 0.66 | 0.038 | 142 | 94  | A | 0.68 |
| Sample No. 13 | Example   | 99 | 5  | 45 | 0.27 | 0.58 | 0.032 | 145 | 93  | A | 0.56 |
| Sample No. 14 | Example   | 93 | 26 | 24 | 0.25 | 0.74 | 0.051 | 77  | 104 | A | 0.47 |
| Sample No. 15 | Example   | 94 | 18 | 18 | 0.26 | 0.76 | 0.062 | 75  | 104 | C | 0.48 |
| Sample No. 16 | Example   | 93 | 20 | 84 | 0.55 | 1.05 | 0.154 | 65  | 109 | C | 0.40 |
| Sample No. 17 | Example   | 96 | 16 | 49 | 0.38 | 0.35 | 0.022 | 54  | 138 | A | 0.83 |
| Sample No. 18 | Example   | 95 | 17 | 66 | 0.16 | 0.45 | 0.121 | 60  | 125 | A | 0.74 |
| Sample No. 19 | Example   | 95 | 18 | 77 | 0.36 | 0.43 | 0.112 | 72  | 116 | A | 0.75 |
| Sample No. 20 | Example   | 92 | 22 | 55 | 0.63 | 0.75 | 0.089 | 198 | 71  | A | 0.41 |
| Sample No. 21 | Example   | 95 | 7  | 19 | 0.37 | 0.75 | 0.063 | 35  | 161 | C | 0.43 |
| Sample No. 22 | Example   | 94 | 6  | 6  | 0.76 | 0.25 | 0.087 | 45  | 157 | C | 0.85 |
| Sample No. 23 | Example   | 95 | 8  | 17 | 0.42 | 0.89 | 0.087 | 28  | 178 | A | 0.41 |
| Sample No. 24 | Example   | 94 | 12 | 15 | 0.48 | 0.97 | 0.097 | 41  | 169 | A | 0.40 |
| Sample No. 25 | Example   | 96 | 11 | 25 | 0.48 | 0.25 | 0.087 | 48  | 146 | C | 0.84 |
| Sample No. 26 | Example   | 95 | 10 | 28 | 0.51 | 1.05 | 0.123 | 72  | 145 | A | 0.40 |
| Sample No. 27 | Comp. Ex. | 85 | 64 | 93 | 0.52 | 15.2 | 1.5   | 38  | 154 | D | —    |
| Sample No. 28 | Comp. Ex. | 84 | 70 | 1  | 0.98 | 12.5 | 1.2   | 22  | 212 | D | —    |
| Sample No. 29 | Comp. Ex. | 87 | 56 | 2  | 1.05 | 10.3 | 1.1   | 26  | 194 | D | —    |

TABLE 4

| | | Dental casting billet material Evaluation results | | | | Cast product | | | | Dental prosthesis Composition | Dental prosthesis Evaluation results |
|---|---|---|---|---|---|---|---|---|---|---|---|
| | | Corrosion resistance — | Meltability Melting time — | Meltability Explosive boiling — | Metal melt fluidity — | 0.2% proof stress MPa | Elongation % | Young's modulus GPa | Castability (appearance) — | of porcelain Alumina content Mass % | Adhesiveness — |
| Sample No. 1  | Example | A | A | A | A | 505 | 40 | >150 | A | 15 | A |
| Sample No. 2  | Example | A | A | A | A | 509 | 38 | >150 | A | 15 | A |
| Sample No. 3  | Example | A | A | A | A | 501 | 33 | >150 | A | 15 | A |
| Sample No. 4  | Example | B | A | A | B | 515 | 22 | >150 | B | 15 | B |
| Sample No. 5  | Example | A | A | B | A | 516 | 42 | >150 | A | 15 | A |
| Sample No. 6  | Example | B | A | C | A | 528 | 17 | >150 | A | 15 | B |
| Sample No. 7  | Example | B | B | D | B | 498 | 9  | >150 | B | 15 | B |
| Sample No. 8  | Example | A | A | B | B | 503 | 36 | >150 | B | 15 | A |
| Sample No. 9  | Example | A | A | A | B | 507 | 41 | >150 | A | 15 | B |
| Sample No. 10 | Example | C | B | D | B | 475 | 8  | >150 | B | 15 | C |
| Sample No. 11 | Example | A | A | A | A | 505 | 40 | >150 | A | 15 | A |
| Sample No. 12 | Example | A | A | A | A | 509 | 38 | >150 | A | 15 | A |
| Sample No. 13 | Example | A | A | A | A | 501 | 33 | >150 | A | 15 | A |
| Sample No. 14 | Example | B | C | A | B | 482 | 22 | >150 | B | 15 | B |
| Sample No. 15 | Example | B | B | A | B | 520 | 15 | >150 | B | 15 | C |
| Sample No. 16 | Example | B | B | A | C | 556 | 7  | >150 | C | 15 | B |
| Sample No. 17 | Example | A | B | A | B | 516 | 32 | >150 | B | 15 | A |
| Sample No. 18 | Example | A | B | B | B | 503 | 36 | >150 | B | 15 | A |
| Sample No. 19 | Example | A | B | A | B | 507 | 41 | >150 | B | 15 | B |
| Sample No. 20 | Example | C | B | D | B | 489 | 6  | >150 | B | 15 | C |
| Sample No. 21 | Example | A | C | A | C | 415 | 7  | —    | C | 15 | B |
| Sample No. 22 | Example | A | C | B | C | 431 | 5  | —    | C | 15 | B |
| Sample No. 23 | Example | C | B | C | B | 335 | 3  | <150 | B | 15 | B |
| Sample No. 24 | Example | C | B | D | B | 342 | 3  | <150 | B | 15 | B |

TABLE 4-continued

|  |  | Dental casting billet material | | | | | | | Cast product | Dental prosthesis | |
|---|---|---|---|---|---|---|---|---|---|---|---|
|  |  | Evaluation results | | | | | | | | Composition | |
|  |  | | Meltability | | | 0.2% | | | | of porcelain | Evaluation |
|  |  | Corrosion resistance | Melting time | Explosive boiling | Metal melt fluidity | proof stress MPa | Elongation % | Young's modulus GPa | Castability (appearance) | Alumina content Mass % | results Adhesiveness |
| Sample No. 25 | Example | A | C | A | C | 445 | 9 | <150 | C | 15 | B |
| Sample No. 26 | Example | D | C | B | C | 398 | 3 | <150 | C | 15 | B |
| Sample No. 27 | Comp. Ex. | D | D | A | D | 326 | 4 | — | D | 15 | D |
| Sample No. 28 | Comp. Ex. | D | D | A | D | 301 | 8 | — | D | 15 | C |
| Sample No. 29 | Comp. Ex. | D | D | A | D | 297 | 12 | — | D | 15 | C |

As apparent from Tables 3 and 4, it was found that each dental casting billet material (Co-based) corresponding to Example has excellent corrosion resistance. Further, it was confirmed that the meltability and the metal melt fluidity are favorable.

Further, it was confirmed that the test piece of the cast product obtained by casting using each dental casting billet material (Co-based) corresponding to Example has excellent mechanical properties and also has few casting defects in appearance.

4. Production of Dental Prosthesis

Each of the dental casting billet materials of the respective sample Nos. was melted, and the obtained metal melt was cast into a mold, whereby a test piece was produced by casting.

Subsequently, an opaque porcelain paste was applied to the surface of the obtained test piece, followed by firing, whereby a test piece of a dental prosthesis was obtained.

As the opaque porcelain paste (alumina content: 15% by mass), "Vintage MP" manufactured by Shofu, Inc. was used. Further, the firing temperature was set to 950° C., and this temperature was maintained for 2 minutes. Further, the firing atmosphere was set to be a reduced pressure atmosphere.

5. Evaluation of Dental Prosthesis

With respect to each of the test pieces of the dental prostheses of the respective sample Nos., a destructive force was applied to the test piece in accordance with the test method for peeling/cracking strength of metal-ceramic dental restorative systems specified in JIS T 6120 (2001), and the adhesiveness of the porcelain layer was evaluated according to the following evaluation criteria.

Evaluation Criteria in Peeling/Cracking Strength Test

A: The strength is more than twice as large as that of the test piece of the sample No. 27.

B: The strength is more than 1.5 times but not more than twice as large as that of the test piece of the sample No. 27.

C: The strength is more than one time but not more than 1.5 times as large as that of the test piece of the sample No. 27.

D: The strength is not more than one time as large as that of the test piece of the sample No. 27.

The above evaluation results are shown in Table 4.

As apparent from Table 4, it was confirmed that each dental prosthesis corresponding to Example has higher adhesiveness of the porcelain layer than each dental prosthesis corresponding to Comparative Example.

Further, each of the dental prostheses corresponding to the respective Examples was cut, and an area analysis of the cross section was performed using an electron probe microanalyzer. As a result, it was confirmed that mullite exists in the form of a layer at the boundary surface between the porcelain layer and the metal frame.

6. Evaluation of Relationship Between Concentration of N and Hardness

First, test pieces of the dental casting billet materials of the respective sample Nos. 30 to 36 having an alloy composition shown in Table 5 were produced.

Subsequently, each of the test pieces was cut, and the cut surface was polished.

Figure 5:
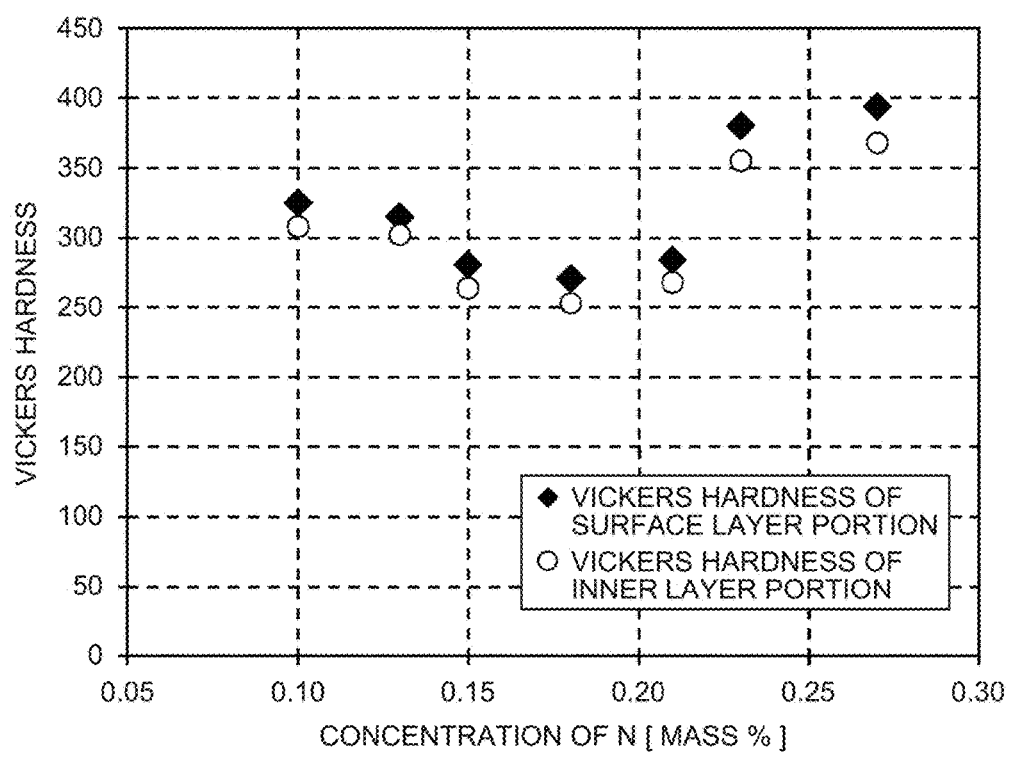
FIG. 5 is a graph showing a relationship between the concentration of N and the Vickers hardness of a surface layer portion and an inner layer portion in test pieces of dental casting billet materials of respective sample Nos. 30 to 36.

Then, the Vickers hardness was measured for a surface layer portion and an inner layer portion in the polished surface. The measurement results are shown in Table 5 and FIG. 5. FIG. 5 is a graph showing a relationship between the concentration of N and the Vickers hardness of the surface layer portion and the inner layer portion in the test pieces of the dental casting billet materials of the respective sample Nos. 30 to 36.

TABLE 5

|  |  | Dental casting billet material | | | | | | | | | |
|---|---|---|---|---|---|---|---|---|---|---|---|
|  |  | | | | | | | | | Evaluation results Vickers hardness | | |
|  |  | Alloy composition | | | | | | | Surface layer | Inner layer | Inner layer portion/surface |
|  |  | Cr | Mo | Si | C Mass % | N | Ni | Co | portion | portion | layer portion % |
| Sample No. 30 | Example | 29.7 | 6.84 | 0.77 | 0.02 | 0.10 | 0.01 | Remainder | 325 | 308 | 95 |
| Sample No. 31 | Example | 29.8 | 6.80 | 0.78 | 0.02 | 0.13 | 0.01 | Remainder | 315 | 302 | 96 |
| Sample No. 32 | Example | 30.2 | 6.82 | 0.79 | 0.02 | 0.15 | 0.01 | Remainder | 281 | 264 | 94 |
| Sample No. 33 | Example | 29.9 | 6.83 | 0.78 | 0.02 | 0.18 | 0.01 | Remainder | 271 | 253 | 93 |
| Sample No. 34 | Example | 30.1 | 6.85 | 0.77 | 0.02 | 0.21 | 0.01 | Remainder | 284 | 268 | 94 |

TABLE 5-continued

| | | Dental casting billet material | | | | | | | Evaluation results Vickers hardness | | |
|---|---|---|---|---|---|---|---|---|---|---|---|
| | | Alloy composition | | | | | | | Surface layer portion | Inner layer portion | Inner layer portion/surface layer portion |
| | | Cr | Mo | Si | C | N | Ni | Co | | | % |
| | | | | | Mass % | | | | — | — | |
| Sample No. 35 | Example | 29.6 | 6.84 | 0.76 | 0.02 | 0.23 | 0.01 | Remainder | 380 | 355 | 93 |
| Sample No. 36 | Example | 29.7 | 6.81 | 0.78 | 0.02 | 0.27 | 0.01 | Remainder | 394 | 368 | 93 |

As apparent from Table 5 and FIG. 5, it was confirmed that there is a relationship between the concentration of N in the test piece and the Vickers hardness such that the hardness becomes minimum at a specific N concentration. As described above, by decreasing the hardness, the toughness of the test piece is increased, and therefore, the tensile strength, the proof stress, and the like can be improved. Further, As a result of the measurement of the concentration of N, even if the total concentration of N was changed, the concentration of N did not differ greatly between the surface layer portion and the inner layer portion.

7. Production of Dental Casting Billet Material (Ni-Based) Sample Nos. 37 to 49

Dental casting billet materials were obtained in the same manner as in the case of the sample No. 1 except that a Ni-based alloy as shown in Table 6 was used as the starting material.

The production conditions for the dental casting billet materials (Ni-based) of the above-mentioned respective sample Nos. are shown in Tables 6 and 7.

TABLE 6

| | | Dental casting billet material Alloy composition | | | | | |
|---|---|---|---|---|---|---|---|
| | | Cr | Mo | Si | C | N | Ni |
| | | | | | Mass % | | |
| Sample No. 37 | Example | 20.8 | 7.80 | 2.28 | 0.02 | 0.13 | Remainder |
| Sample No. 38 | Example | 18.3 | 9.42 | 2.46 | 0.04 | 0.18 | Remainder |
| Sample No. 39 | Example | 19.5 | 8.31 | 2.33 | 0.03 | 0.12 | Remainder |
| Sample No. 40 | Example | 17.1 | 6.41 | 1.84 | 0.02 | 0.09 | Remainder |
| Sample No. 41 | Example | 22.9 | 7.35 | 2.21 | 0.07 | 0.23 | Remainder |
| Sample No. 42 | Example | 24.5 | 10.03 | 2.15 | 0.13 | 0.28 | Remainder |
| Sample No. 43 | Example | 25.9 | 12.05 | 2.45 | 0.35 | 0.27 | Remainder |
| Sample No. 44 | Example | 18.1 | 6.58 | 2.46 | 0.07 | 0.11 | Remainder |
| Sample No. 45 | Example | 17.1 | 6.74 | 2.33 | 0.04 | 0.12 | Remainder |
| Sample No. 46 | Example | 20.9 | 11.25 | 2.15 | 1.19 | 0.21 | Remainder |
| Sample No. 47 | Comp. Ex. | 20.2 | 7.21 | 2.15 | 0.04 | 0.32 | Remainder |
| Sample No. 48 | Comp. Ex. | 18.9 | 6.35 | 2.19 | 0.02 | 0.45 | Remainder |
| Sample No. 49 | Comp. Ex. | 21.1 | 7.54 | 2.11 | 0.05 | 0.39 | Remainder |

TABLE 7

| | | Dental casting billet material | | | | | |
|---|---|---|---|---|---|---|---|
| | | Alloy composition | | | | | |
| | | Si/Mo | C/Si | N/Si | N/C | N impregnation method | Molding method |
| Sample No. 37 | Example | 0.292 | 0.009 | 0.057 | 6.50 | Nitriding of metal material | Powder metallurgy |
| Sample No. 38 | Example | 0.261 | 0.016 | 0.073 | 4.50 | Nitriding of metal material | Powder metallurgy |
| Sample No. 39 | Example | 0.280 | 0.013 | 0.052 | 4.00 | Nitriding of metal material | Powder metallurgy |
| Sample No. 40 | Example | 0.287 | 0.011 | 0.049 | 4.50 | Nitriding of metal material | Powder metallurgy |
| Sample No. 41 | Example | 0.301 | 0.032 | 0.104 | 3.29 | Nitriding of metal material | Powder metallurgy |
| Sample No. 42 | Example | 0.214 | 0.060 | 0.130 | 2.15 | Nitriding of metal material | Powder metallurgy |
| Sample No. 43 | Example | 0.203 | 0.143 | 0.110 | 0.77 | Nitriding of metal material | Powder metallurgy |
| Sample No. 44 | Example | 0.374 | 0.028 | 0.045 | 1.57 | Nitriding of metal material | Powder metallurgy |
| Sample No. 45 | Example | 0.346 | 0.017 | 0.052 | 3.00 | Nitriding of metal material | Powder metallurgy |
| Sample No. 46 | Example | 0.191 | 0.553 | 0.098 | 0.18 | Nitriding of metal material | Powder metallurgy |
| Sample No. 47 | Comp. Ex. | 0.298 | 0.019 | 0.149 | 8.00 | Injection into metal melt | Casting |
| Sample No. 48 | Comp. Ex. | 0.345 | 0.009 | 0.205 | 22.50 | Injection into metal melt | Casting |
| Sample No. 49 | Comp. Ex. | 0.280 | 0.024 | 0.185 | 7.80 | Injection into metal melt | Casting |

In the respective tables, among the metal powders and the dental casting billet materials of the respective sample Nos., those corresponding to the invention are indicated by "Example", and those not corresponding to the invention are indicated by "Comp. Ex." (Comparative Example).

8. Evaluation of Dental Casting Billet Material (Ni-Based)

With respect to each of the dental casting billet materials (Ni-based) of the respective sample Nos., various evaluations were performed in the same manner as the abovementioned "2. Evaluation of Dental Casting Billet Material (Co-based)". The evaluation results are shown in Tables 8 and 9.

In the evaluation of adhesiveness of a porcelain layer of each of the test pieces of the dental prostheses, the test piece of the sample No. 47 was used as a reference standard for the evaluation.

Further, with respect to "2.4 Evaluation of Crystal Structure by X-ray Diffractometry", the implementation of the evaluation was omitted.

sponding to Example has favorable corrosion resistance, meltability, and metal melt fluidity in the same manner as in the case of Co-base dental casting billet material.

Further, it was confirmed that the test piece of the cast product obtained by casting using each dental casting billet material (Ni-based) corresponding to Example has excellent mechanical properties, and also has few casting defects in appearance.

What is claimed is:
1. A dental casting billet material, comprising:
   Co as a main component;
   Cr in a proportion of 26% by mass or more and 35% by mass or less;
   Mo in a proportion of 5% by mass or more and 12% by mass or less; and
   Si in a proportion of 0.3% by mass or more and 2.0% by mass or less,
   wherein the billet material is formed from a sintered body of a metal powder,
   the billet material has a relative density of 92% or more and 99.5% or less,

TABLE 8

| | | Dental casting billet material Evaluation results | | | | | | | | |
|---|---|---|---|---|---|---|---|---|---|---|
| | | | | | Pore | | Inner layer portion/surface layer portion | | | |
| | | Relative density % | Crystal grain diameter μm | $SiO_2$/total Si % | Average diameter μm | Area ratio % | N concentration % | Hardness % | Dendrite phase | Aspect ratio |
| Sample No. 37 | Example | 95 | 8 | 55 | 0.55 | 0.028 | 105 | 99 | B | 0.77 |
| Sample No. 38 | Example | 96 | 7 | 38 | 0.63 | 0.045 | 121 | 97 | A | 0.56 |
| Sample No. 39 | Example | 95 | 9 | 49 | 0.54 | 0.051 | 94 | 103 | B | 0.59 |
| Sample No. 40 | Example | 94 | 13 | 26 | 0.77 | 0.032 | 76 | 104 | C | 0.64 |
| Sample No. 41 | Example | 99 | 6 | 52 | 0.36 | 0.044 | 132 | 97 | A | 0.87 |
| Sample No. 42 | Example | 98 | 8 | 34 | 0.87 | 0.078 | 110 | 96 | A | 0.45 |
| Sample No. 43 | Example | 96 | 10 | 29 | 0.95 | 0.102 | 175 | 89 | A | 0.42 |
| Sample No. 44 | Example | 93 | 13 | 68 | 0.43 | 0.135 | 68 | 112 | C | 0.77 |
| Sample No. 45 | Example | 94 | 14 | 75 | 0.45 | 0.154 | 97 | 98 | B | 0.74 |
| Sample No. 46 | Example | 92 | 26 | 56 | 0.77 | 0.115 | 105 | 97 | A | 0.45 |
| Sample No. 47 | Comp. Ex. | 82 | 75 | 92 | 19.6 | 2.3 | 37 | 156 | D | — |
| Sample No. 48 | Comp. Ex. | 91 | 72 | 2 | 17.5 | 1.8 | 25 | 208 | D | — |
| Sample No. 49 | Comp. Ex. | 84 | 63 | 7 | 13.6 | 1.6 | 24 | 187 | D | — |

TABLE 9

| | | Dental casting billet material Evaluation results | | | | Cast product | | | | Dental prosthesis Composition of porcelain | Evaluation results |
|---|---|---|---|---|---|---|---|---|---|---|---|
| | | Corrosion resistance — | Meltability | | Metal melt fluidity — | 0.2% proof stress MPa | Elongation % | Young's modulus GPa | Castability (appearance) — | Alumina content Mass % | Adhesiveness — |
| | | | Melting time — | Explosive boiling — | | | | | | | |
| Sample No. 37 | Example | A | A | A | A | 485 | 38 | >150 | A | 15 | A |
| Sample No. 38 | Example | A | A | A | A | 489 | 36 | >150 | A | 15 | A |
| Sample No. 39 | Example | A | A | A | A | 481 | 31 | >150 | A | 15 | A |
| Sample No. 40 | Example | B | A | A | B | 495 | 20 | >150 | B | 15 | B |
| Sample No. 41 | Example | A | A | B | A | 496 | 38 | >150 | A | 15 | A |
| Sample No. 42 | Example | B | A | C | A | 508 | 16 | >150 | A | 15 | B |
| Sample No. 43 | Example | B | B | C | B | 520 | 10 | >150 | B | 15 | B |
| Sample No. 44 | Example | A | A | B | B | 502 | 34 | >150 | B | 15 | A |
| Sample No. 45 | Example | A | A | A | B | 501 | 42 | >150 | A | 15 | B |
| Sample No. 46 | Example | C | B | C | B | 499 | 7 | >150 | B | 15 | C |
| Sample No. 47 | Comp. Ex. | D | D | A | D | 316 | 5 | — | D | 15 | D |
| Sample No. 48 | Comp. Ex. | D | D | A | D | 287 | 7 | — | D | 15 | C |
| Sample No. 49 | Comp. Ex. | D | D | A | D | 274 | 11 | — | D | 15 | C |

As apparent from Tables 8 and 9, it was confirmed that also each dental casting billet material (Ni-based) correa part of the Si is contained as silicon oxide, and
the ratio of Si contained as the silicon oxide to the Si is 10% by mass or more and 90% by mass or less.

2. The dental casting billet material according to claim 1, wherein the silicon oxide is segregated at a grain boundary of the sintered body.

3. The dental casting billet material according to claim 1, wherein the average diameter of crystal structures is 3 μm or more and 50 μm or less.

4. The dental casting billet material according to claim 1, further comprising C in a proportion of 0.01% by mass or more and 0.09% by mass or less.

5. The dental casting billet material according to claim 4, further comprising N in a proportion 0.3 times or more and 10 times or less of the content of C in terms of mass ratio.

6. A metal powder for powder metallurgy, comprising:
Co as a main component;
Cr in a proportion of 26% by mass or more and 35% by mass or less;
Mo in a proportion of 5% by mass or more and 12% by mass or less; and
Si in a proportion of 0.3% by mass or more and 2.0% by mass or less,
wherein the metal powder is used for producing a dental member,
a part of the Si is contained as silicon oxide, and
the ratio of Si contained as the silicon oxide to the Si is 10% by mass or more and 90% by mass or less.

7. A dental metal component, comprising:
Co as a main component;
Cr in a proportion of 26% by mass or more and 35% by mass or less;
Mo in a proportion of 5% by mass or more and 12% by mass or less; and
Si in a proportion of 0.3% by mass or more and 2.0% by mass or less,
wherein the dental metal component is obtained by melting and casting a dental member, which is formed from a sintered body of a metal powder, and has a relative density of 92% or more and 99.5% or less,
a part of the Si is contained as silicon oxide, and
the ratio of Si contained as the silicon oxide to the Si is 10% by mass or more and 90% by mass or less.

* * * * *